(12) United States Patent
Arai et al.

(10) Patent No.: US 7,039,156 B2
(45) Date of Patent: May 2, 2006

(54) DISPLAY METHOD AND APPARATUS OF X-RAY PROJECTION IMAGE FOR MEDICAL USE, X-RAY CT APPARATUS FOR MEDICAL USE AND RECORDING MEDIUM FOR RECORDING PROGRAM TO ACHIEVE THE DISPLAY METHOD

(75) Inventors: Yoshinori Arai, Tokyo (JP); Masakazu Suzuki, Kyoto (JP); Kouji Yasuda, Kyoto (JP)

(73) Assignees: Nihon University, Tokyo (JP); J. Morita Manufacturing Corporation, Kyoto (JP)

( * ) Notice: Subject to any disclaimer, the term of this patent is extended or adjusted under 35 U.S.C. 154(b) by 184 days.

(21) Appl. No.: 10/398,321

(22) PCT Filed: Oct. 4, 2001

(86) PCT No.: PCT/JP01/08740

§ 371 (c)(1),
(2), (4) Date: Jul. 7, 2003

(87) PCT Pub. No.: WO02/28285

PCT Pub. Date: Apr. 11, 2002

(65) Prior Publication Data

US 2004/0066877 A1 Apr. 8, 2004

(30) Foreign Application Priority Data

Oct. 4, 2000 (JP) .................................... 2000-304540

(51) Int. Cl.
*A61B 6/14* (2006.01)

(52) U.S. Cl. ............................... 378/39; 378/38; 378/22

(58) Field of Classification Search ...................... 378/4, 378/8, 15, 22, 23, 38, 39
See application file for complete search history.

(56) References Cited

U.S. PATENT DOCUMENTS 5,214,686 A * 5/1993 Webber ........................ 378/38

* cited by examiner

*Primary Examiner*—David V Bruce
(74) *Attorney, Agent, or Firm*—Koda & Androlia

(57) ABSTRACT

A display method and apparatus of an X-ray projection image for medical use wherein a projection interested area to construct the X-ray projection image of an object is set on an image layer with an extending predetermined thickness perpendicular to an X-ray radiation plane defined by rotational radiation of an X-ray beam, the projection interested area is comprised of the three dimensional X-ray absorption coefficient data, and the X-ray projection image is produced by projecting the three dimensional X-ray absorption coefficient data existing in the projection interested area with respect to a projection plane intersecting the X-ray radiation plane.

40 Claims, 22 Drawing Sheets cheek side all area tongue side cheek side all area tongue side

DISPLAY METHOD AND APPARATUS OF X-RAY PROJECTION IMAGE FOR MEDICAL USE, X-RAY CT APPARATUS FOR MEDICAL USE AND RECORDING MEDIUM FOR RECORDING PROGRAM TO ACHIEVE THE DISPLAY METHOD

TECHNICAL FIELD

The present invention relates to a display method of an X-ray projection image for medical use based on three dimensional X-ray absorption coefficient data obtained by an X-ray computed tomography (called CT hereinafter) method in which an X-ray image of an object to be examined is obtained by turning an X-ray generator and an X-ray detector faced each other, to its display apparatus, to an X-ray CT apparatus using the display method and a recording medium for recording a program to achieve the display method.

BACKGROUND ART

The applicants have proposed an X-ray CT method and apparatus in which conical X-ray beams with remarkably small sectional radiation area are locally radiated only on a local region, a part of an object, to obtain clear three dimensional X-ray absorption coefficient data on the region. For example, JP-A-2000-139902 discloses its CT method and apparatus.

In this laid open publication, the applicants have proposed a basic X-ray CT method in which a rotation center of a rotary arm with an X-ray generator and an X-ray detector faced each other was set on a center of a local region of an object, conical X-ray beams are locally radiated all around or half around a circumference of the object to obtain transmitted data, and the obtained transmitted images are backprojected to obtain three dimensional X-ray absorption coefficient data of the local region. Also they have proposed a method to obtain an X-ray panoramic image of a dental arch in the dental field using the above-mentioned CT method in which a clear X-ray panoramic image could be obtained with a small amount of X-ray exposure and a short radiation time.

However, such obtained X-ray panoramic image included obstacle shades such as a neck bone which existed on the radiation orbit of a conical X-ray beam other than the dental arch like a prior film-type X-ray panoramic images. Therefore, improvement of clearness of images has been desired. Further, the panoramic images were generally used images for diagnosis in the dental field, however they weren't easily understood by intuition as a dental arch was actually seen from one direction. Although the condition of a dental root could be understood by the obtained X-ray panoramic images, it was difficult to distinguish where the root exists from a cheek to a tongue.

DISCLOSURE OF THE INVENTION

The present invention is proposed to solve the above-mentioned problems. The object of the present invention is to provide a display method and apparatus for medical use for showing X-ray projection images which have less obstacle shades and less X-ray exposure amount, are easily understood by intuition for medical use, are useful for diagnosis and show where a dental root exists from a cheek to a tongue while utilizing several advantages of local X-ray CT method and apparatus on a local region and obtained three dimensional X-ray absorption coefficient data. And other object of the present invention is to provide an X-ray CT apparatus for medical use using this display method and to provide a recording medium for recording a program to achieve the display method. The following items (1)–(11) propose a display method of X-ray projection images for medical use, (12)–(21) propose a display apparatus to achieve the display method, (22)–(29) propose an X-ray CT apparatus for medical use using the display method, and (30)–(40) propose a recording medium for recording a program to achieve the display method.

(1) This display method of X-ray projection images for medical use is characterized in that, without using three dimensional X-ray absorption coefficient data obtained by an X-ray CT as it is for constructing an X-ray projection image, three dimensional X-ray absorption coefficient data are extracted on an image layer having a predetermined thickness in a direction perpendicular to an X-ray radiation plane, namely on the image wherein three dimensional X-ray absorption coefficient data are seen from a rotation axial direction of X-ray radiation and a projection interested area to construct an X-ray projection image is set.

For example, clear border lines of all over the horizontal direction of a dental arch aren't obtained by such image layer, however, border lines which may specify the position of the dental arch, or border lines which may specify the position of obstacle shades such as neck bone can be obtained. Thus, only the dental arch area including the dental arch is set to be a projection interested area on the layer, thus obtaining an X-ray projection image without obstacle shades.

According to this display method, a projection plane to be projected with an X-ray projection image is set to be a flat surface intersecting a radiation plane, in particular substantially perpendicular to an X-ray radiating direction. And an X-ray projection image is obtained by projecting three dimensional X-ray absorption coefficient data in the projection interested area with respect to the projection plane and the obtained X-ray projection image is displayed.

In such a manner, three dimensional X-ray absorption coefficient data existing in a direction substantially along the X-ray radiating direction so that clear images can be obtained. In addition, three dimensional X-ray absorption coefficient data are projected on the flat projection plane. Therefore, exemplifying a dental arch, images seen from a projecting direction perpendicular to the projection plane can be obtained and they are easily comprehensive images by intuition for dental diagnosis. Further, perspectively observable image like the dental arch, namely an object to be examined, is turned by sequentially obtaining and displaying X-ray projection images by rotating a direction in which the X-ray projection image is to be projected, that is the projection plane, thus obtaining highly comprehensive and highly advantageous images for diagnosis.

According to the method wherein the above-mentioned local X-ray CT method is applied to obtain an X-ray panoramic image of a dental arch in the dental field, a rotation center of a rotary arm is fixed around a median line inside of the dental arch and only a local region around the rotation center is always locally radiated. In this case, X-rays are radiated on each tooth of the dental arch only in a limited directional area, namely a directional area limited like in a generally used film type X-ray panoramic radiation.

Therefore, when this display method is applied to the three dimensional X-ray absorption coefficient data obtained by a method wherein the local X-ray CT method is applied to panoramic images, both effects are multiplied so that several advantages of local X-ray CT method and apparatus can be used.

(2) Comparing with the method (1), this display method of X-ray projection images for medical use is characterized in that not only one X-ray projection image obtained by the method (1) is shown but also plural X-ray projection images can be shown in array. Therefore, in addition to the effects of (1), X-ray projection images in which an object such as a dental arch is seen from different directions can be compared each other and be compared in a list to select an image required for diagnosis because of such plural displaying, therefore being convenient.

(3) Comparing with the method (1), this display method of X-ray projection images for medical use can show the object in a rotational manner (in a manner that the object is rotated) by continuously showing the X-ray projection images obtained by the method (1) while changing the projecting directions. Therefore, in addition to the effects of (1), even if the display screen is limited, the X-ray projection images of an object such as a dental arch can be continuously compared to select a necessary image for diagnosis because of the continuous rotary display of the X-ray projection images which are easily comprehended by intuition. Accordingly, this method is convenient.

(4) Comparing with the method (1), this display method of X-ray projection images for medical is characterized in that the projection interested area is in advance divided into several projection interested layers neighboring each other considering an X-ray radiating direction, three dimensional X-ray absorption coefficient data in optional one layer or the neighboring plural layers are used and thus obtained X-ray projection images are selectively displayed. Therefore, in addition to the effects of (1), if the projection interested area is a dental arch area, the projection interested layer is a layer neighboring each other from a cheek to a tongue. Thus knowing the image layer used for constructing the X-ray projection image of the dental root, the position of the root where in a cheek to a tongue can be understood.

(5) Comparing with the method (1), this display method of X-ray projection images for medical use combines the display in array in (2), the continuous display in (3) and the display method in (4) wherein the projection interested area is divided into plural projection interested layers and the X-ray projection images obtained by using the three dimensional X-ray absorption coefficient data in the projection interested layer are selectively shown. Therefore, the effects of (2), (3) and (4) are multiplied in addition to the effect of (1).

(6) This display method of X-ray projection images for medical use particularly defines the projection interested area of the above-mentioned display methods into a dental arch area. Therefore, the above-mentioned effects can be achieved for displaying the X-ray projection image of the dental arch area.

(7) According to this display method of X-ray projection images for medical use, in case that the projection interested area is a dental arch area, the projection plane is arranged to be parallel to a rising direction of a tooth or a projecting direction of a dental root in the dental arch area. The rising direction of a tooth isn't always a direction perpendicular to an articulation surface of the dental arch, namely a direction orthogonal to a projecting direction of X-ray. Therefore, if a projection plane is normally set, an X-ray projection image showing a rising direction of a dental tooth at an angle is obtained and the accurate length of the tooth in a rising direction isn't shown in the image. However, if the projection plane is parallel to the rising direction of the tooth, the rising length of the tooth is accurately shown on the image, thus improving convenience.

(8) In this display method of X-ray projection images for medical use, when the projection interested area is a dental arch area, a rotation center of a projection plane which is rotatively moved is fixed. In such a manner, even in a method a local X-ray CT method is applied to panoramic images, when a rotation center of a rotary arm is fixed at the time of projection, control is facilitated. Otherwise, a rotary arm may be moved in case of projection.

(9) In this display method of X-ray projection images for medical use, a rotation center of the projection plane which is rotatively moved is transferred in a predetermined pattern in the above-mentioned display methods (5)–(7) wherein the projection interested area is a dental arch area. In this case, if a rotation center of a rotary arm isn't fixed during projection when the local X-ray CT method is applied to panoramic images, clear X-ray projection images can be obtained by conforming radiating conditions and projecting conditions. When a rotation center of a rotary arm is fixed during projection, obstacle shades such as a neck bone can be eliminated.

(10) In this display method of X-ray projection images for medical use, a method characterized in that a projection interested area is set and three dimensional X-ray absorption coefficient data in the area are projected is applied to produce X-ray panoramic images. Therefore, images without obstacle shades are also obtained for X-ray panoramic images.

The projection plane for producing X-ray panoramic images is curved unlike the flat projection plane in (1). If an object is a dental arch, the curved projection plane is a curved plane binding the center of each tooth. These X-ray panoramic images aren't only used for a dental arch in the dental field, but they include X-ray projection images used for other medical field such as diagnosis of rib bone in addition to an otolaryngology area, a dental surgery area, and a maxillo facial area to obtain images by sequentially projecting on the curved projection plane.

(11) In this display method of X-ray projection images for medical use, the display method characterized in that a projection interested area is divided into projection interested layers and the X-ray projection images obtained by three dimensional X-ray absorption coefficient data in the projection interested layer are selectively displayed is applied to X-ray panoramic images. Therefore, as to X-ray panoramic images, where a dental root exists from a cheek to a tongue can be understood.

(12) This display apparatus of X-ray projection images for medical use is to achieve the above-mentioned display methods (1) and (2). Therefore, it has the same effect as (1) and (2). Further, the X-ray projection images which have been once stored are read out to be displayed so that the X-ray projection images aren't required to be produced each time. Therefore, the X-ray projection images can be promptly displayed, thus preventing an operator from being annoyed to wait for a display required for diagnosis.

(13) This display apparatus of X-ray projection images for medical use is to achieve the above-mentioned display method (3). Therefore, it has the same effect as (3). Further, the X-ray projection images which have been once stored are read out to be displayed so that the X-ray projection images aren't required to be produced each time. Therefore, the X-ray projection images can be promptly displayed, thus preventing an operator from being annoyed to wait for display required for diagnosis.

(14) This display apparatus of X-ray projection images for medical use is to achieve the above-mentioned display method (4). Therefore, it has the same effect as (4). Further, the X-ray projection images which have been once stored are read out to be displayed so that the X-ray projection images aren't required to be produced each time. Therefore, the X-ray projection images can be promptly displayed, thus preventing an operator from being annoyed to wait for display required for diagnosis.

(15) This display apparatus of X-ray projection images for medical use is to achieve the display method in the above-mentioned (5). Therefore, it has the same effect as (5). Further, the X-ray projection images which have been once stored are read out to be displayed so that the X-ray projection images aren't required to be produced each time. Therefore, the X-ray projection images can be promptly displayed, thus preventing an operator from being annoyed to wait for display required for diagnosis.

(16) This display apparatus of X-ray projection images for medical use is to achieve the above-mentioned display method (6). Therefore, it has the same effect as (6).

(17) This display apparatus of X-ray projection images for medical use is to achieve the above-mentioned display method (7). Therefore, it has the same effect as (7).

(18) This display apparatus of X-ray projection images for medical use is to achieve the above-mentioned display method (8). Therefore, it has the same effect as (8).

(19) This display apparatus of X-ray projection images for medical use is to achieve the above-mentioned display method (9). Therefore, it has the same effect as (9).

(20) This display apparatus of X-ray projection images for medical use is to achieve the display method in the above-mentioned (10). Therefore, it has the same effect as (10).

(21) This display apparatus of X-ray projection images for medical use is to achieve the above-mentioned display method (11). Therefore, it has the same effect as (11).

(22) In this X-ray CT apparatus for medical use, an image construction means having an X-ray generator and an X-ray detector is combined with the display method (15). It achieves the display method (5) and has the effect of (5) as a medical X-ray CT apparatus.

(23) This X-ray CT apparatus for medical use achieves the display method in (6) and has the effect of (6).

(24) This X-ray CT apparatus for medical use is for obtaining X-ray panoramic images, achieves the display methods in (10) and (11) and has the effects of (10) and (11).

(25) According to this X-ray CT apparatus for medical use, a rotation center of a rotary arm is moved, not being fixed during X-ray radiation. For example if a rotation center of radiated X-rays is moved along an envelope curve, X-rays can be radiated on a dental arch from a direction substantially perpendicular to a tooth, thereby achieving valuable images for diagnosis without obstacle shades.

(26) According to this X-ray CT apparatus for medical use, comparing with the apparatus (25), a rotation center of a rotary arm is fixed, an object is gradually moved during X-ray radiation, thus a rotation center of the radiated X-rays is relatively moved. In addition to the same effect as (25), more precise X-ray radiation can be accomplished because the rotation center of the rotary arum isn't moved. More accurate three dimensional X-ray absorption coefficient data can be obtained from thus obtained transmitted data and as the result more accurate X-ray projection image can be also obtained.

(27) According to this X-ray CT apparatus for medical use, X-rays are radiated while varying a rotational speed of a rotary arm. Therefore, density compensation can be executed according to the radiated tooth, thus obtaining better X-ray projection images.

(28) According to this X-ray CT apparatus for medical use, like the apparatus (27), density compensation can be executed according to the radiated tooth, thus obtaining better X-ray projection images.

(29) According to this X-ray CT apparatus for medical use, inclination of a chair for holding an object is adjusted in such a manner that an X-ray radiating direction becomes, for example, perpendicular to a rising direction of a tooth, thereby obtaining transmitted images without inclining the rising direction of a tooth. Accordingly, better X-ray projection images reflecting the rising direction of a tooth can be obtained.

(30) This recording medium saves a program to achieve the display method (1). When the medium reads the program and is attached to an apparatus capable of carrying out the program, the display method (1) is achieved and the effect of (1) is brought out.

(31) This recording medium saves a program to achieve the display method (2). When the medium reads the program and is attached to an apparatus capable of carrying out the program, the display method (2) is achieved and the effect of (2) is brought out.

(32) This recording medium saves a program to achieve the display method (3). When the medium reads the program and is attached to an apparatus capable of carrying out the program, the display method (3) is achieved and the effect of (3) is brought out.

(33) This recording medium saves a program to achieve the display method (4). When the medium reads the program and is attached to an apparatus capable of carrying out the program, the display method (4) is achieved and the effect of (4) is brought out.

(34) This recording medium saves a program to achieve the display method (5). When the medium reads the program and is attached to an apparatus capable of carrying out the program, the display method (5) is achieved and the effect of (5) is brought out.

(35) This recording medium saves a program to achieve the display method (6). When the medium reads the program and is attached to an apparatus capable of carrying out the program, the display method (6) is achieved and the effect of (6) is brought out.

(36) This recording medium saves a program to achieve the display method (7). When the medium reads the program and is attached to an apparatus capable of carrying out the program, the display method (7) is achieved and the effect of (7) is brought out.

(37) This recording medium saves a program to achieve the display method (8). When the medium reads the program and is attached to an apparatus capable of carrying out the program, the display method (8) is achieved and the effect of (8) is brought out.

(38) This recording medium saves a program to achieve the display method (9). When the medium reads the program and is attached to an apparatus capable of carrying out the program, the display method (9) is achieved and the effect of (9) is brought out.

(39) This recording medium saves a program to achieve the display method (10). When the medium reads the program and is attached to an apparatus capable of carrying out the program, the display method (10) is achieved and the effect of (10) is brought out.

(40) This recording medium saves a program to achieve the display method (11). When the medium reads the program and is attached to an apparatus capable of carrying out the program, the display method (11) is achieved and the effect of (11) is brought out.

BRIEF DESCRIPTION OF DRAWINGS

In FIG. 14 the X-ray radiation method in FIG. 13 is applied to other teeth.

BEST MODE FOR CARRYING OUT THE INVENTION

Figure 1A:
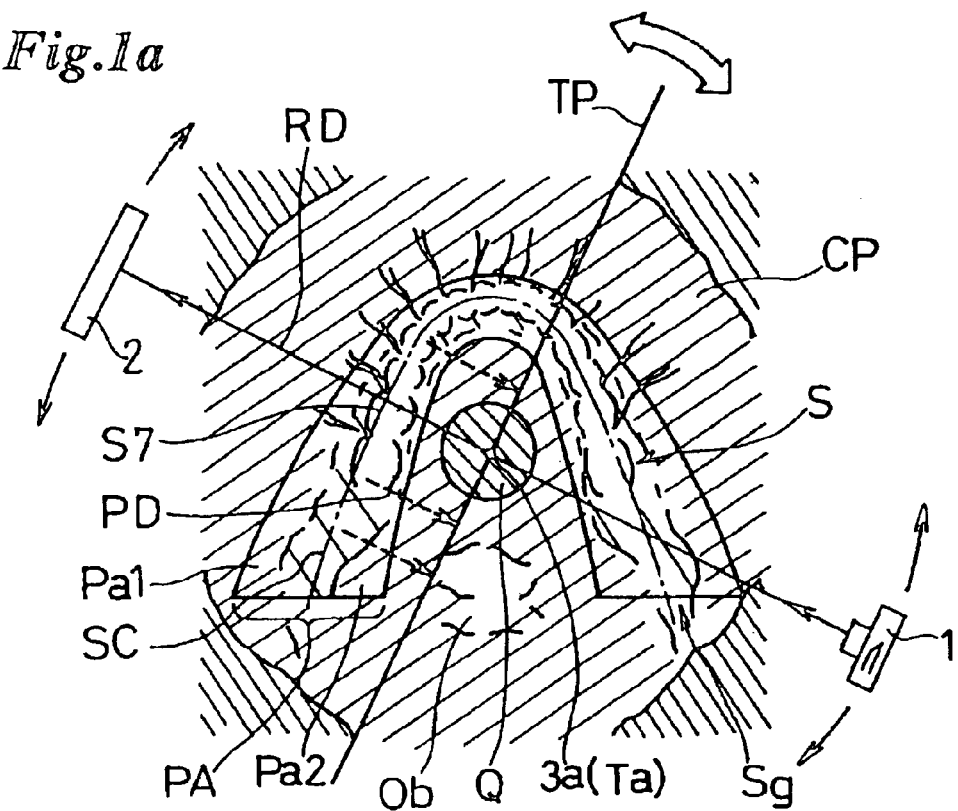
FIG. 1a is a conceptual diagram explaining a procedure of a display method of X-ray projection images for medical use according to the present invention.
Figure 1B:
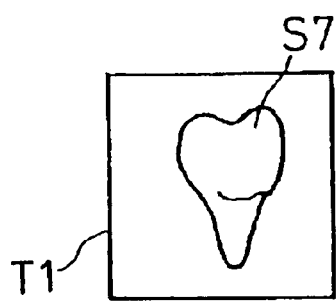
FIGS. 1b, 1c and 1d show an example of X-ray projection images of a tooth shown according to the method.
Figure 1C:
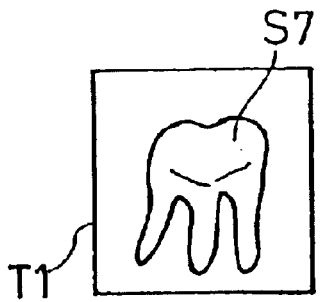
Figure 1D:
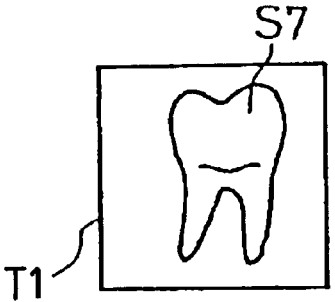

FIG. 1a is a conceptual diagram explaining a procedure of a display method of X-ray projection images for medical use according to the present invention, FIGS. 1b, 1c and 1d show an example of X-ray projection images of a tooth shown according to the method.

FIG. 1a shows an image wherein three dimensional X-ray absorption coefficient data obtained by an X-ray CT method in which an X-ray generator 1 and an X-ray detector 2 are opposed and rotated around a dental arch S, being an object to be examined, are seen from an image layer CP having a predetermined thickness in a direction perpendicular to a radiated plane obtained by rotation of X-ray radiation, namely shows an image when three dimensional X-ray absorption coefficient data are seen from an axial direction of a rotation center 3a of X-ray radiation.

Circular area around the center of the image layer CP is called as a virtual local region Q which is always locally radiated with X-rays in a radiography wherein a local X-ray CT method is applied to panoramic images as mentioned hereinafter. When an object is a dental arch S, the region Q is generally selected around a median line inside of the dental arch. Here in this specification, the virtual local region Q and the areas around four corners of the figure are eliminated from the area to calculate three dimensional X-ray absorption coefficient data to be left as more density parts.

According to the display method of X-ray projection images for medical use of the present invention, a projection interested area PA to construct the X-ray projection images of the object, namely a dental arch S in this specification, is set under the following procedures.

<Setting of Projection Interested Area PA>

1. As shown in FIG. 1a, the image of the image layer CP is displayed.
2. Border lines of the dental arch S and a jawbone Sg are appeared on the image layer CP, although unclear, in such a manner their position on a radiated plane can be specified. A dental arch area to extract three dimensional X-ray absorption coefficient data is defined aiming at the border lines so as to include the dental arch S and its supporting alveolar therearound.
3. Each specific point on the border lines of the projection interested area PA in the figure is specified, for example, on the image of the image layer CP by means of a pointing device such as a mouse (not shown) and the points are combined with a line so as to be compensated, thereby achieving setting. Dental arch area pattern calculated from the past statistical data is applied per the kinds of the object, for example age and sex, thereby achieving setting.
4. In this case, as shown in the figure, such parts as a neck bone being an obstacle shade Ob in the projection interested area PA are designed to be eliminated.

Thus the projection interested area PA is set in advance, three dimensional X-ray absorption coefficient data only in this area PA are used for projection, and X-ray projection images without obstacle shades Ob can be obtained.

Then, the projection interested area PA is divided into plural projection interested layers Pa1 and Pa2 which are adjacent each other in a direction of an X-ray radiating direction RD. Here the dental arch area is set as a projection interested area PA and the area PA is divided into two parts Pa1 which is a cheek side and Pa2 which is a tongue side by a center line SC of the dental arch. The setting method of the center line SC of the dental arch is the same as that of the projection interested area PA. If a shape of the projection interested area PA is once determined, sometimes all required is to specify the thickness of the produced projection interested layer in order to divide the area PA into plural projection interested layers adjacent each other in the X-ray radiating direction RD at each area PA.

As shown in the figure, for obtaining the X-ray projection image of a tooth S7 of the dental arch S, a projection plane TP intersecting the X-ray radiating direction RD from which the tooth S7 is radiated is set. The projection plane TP is thus set and only effective three dimensional X-ray absorption coefficient data aligning along the X-ray radiating direction RD are projected on the projection plane TP, thus obtaining clear X-ray projection images.

After the projection plane TP is set, the three dimensional X-ray absorption coefficient data in the projection interested area PA are projected on the projection plane TP only from the projection plate side, in this case from the opposite side of the X-ray radiating direction RD against the projection plane TP. Then the X-ray projection image TI of the tooth S7 as shown in FIG. 1c can be obtained.

Although it can be understood there exist three dental roots on the X-ray projection image TI of the tooth S7, it is difficult to determine whether those roots exist in a cheek side or in a tongue side. In this case, the X-ray projection image using the projection interested layers Pa1 and Pa2 is helpful.

When the three dimensional X-ray absorption coefficient data of the projection interested layer Pa1 at cheek side is projected on the projection plane TP, the X-ray projection image TI of the tooth S7 shown in FIG. 1b can be obtained. When the three dimensional X-ray absorption coefficient data of the projection interested layer Pa2 at tongue side is projected on the projection plane TP, the X-ray projection image TI of the tooth S7 shown in FIG. 1d can be obtained. From the X-ray projection images TI shown in FIGS. 1b and 1d, it is understood that there is one root at cheek side and other two roots are at tongue side.

Exemplifying a dental arch as mentioned above, what exists in which image layer can be understood as an X-ray projection image by dividing the projection interested area PA into plural projection interested layers Pa, that is for example a dental root exists where in the cheek side to the tongue side.

More detailed positional detection is possible by appropriately selecting a projection interested area PA at first. Further it is also possible by dividing the area into a larger number of projection interested layers.

Figure 2:
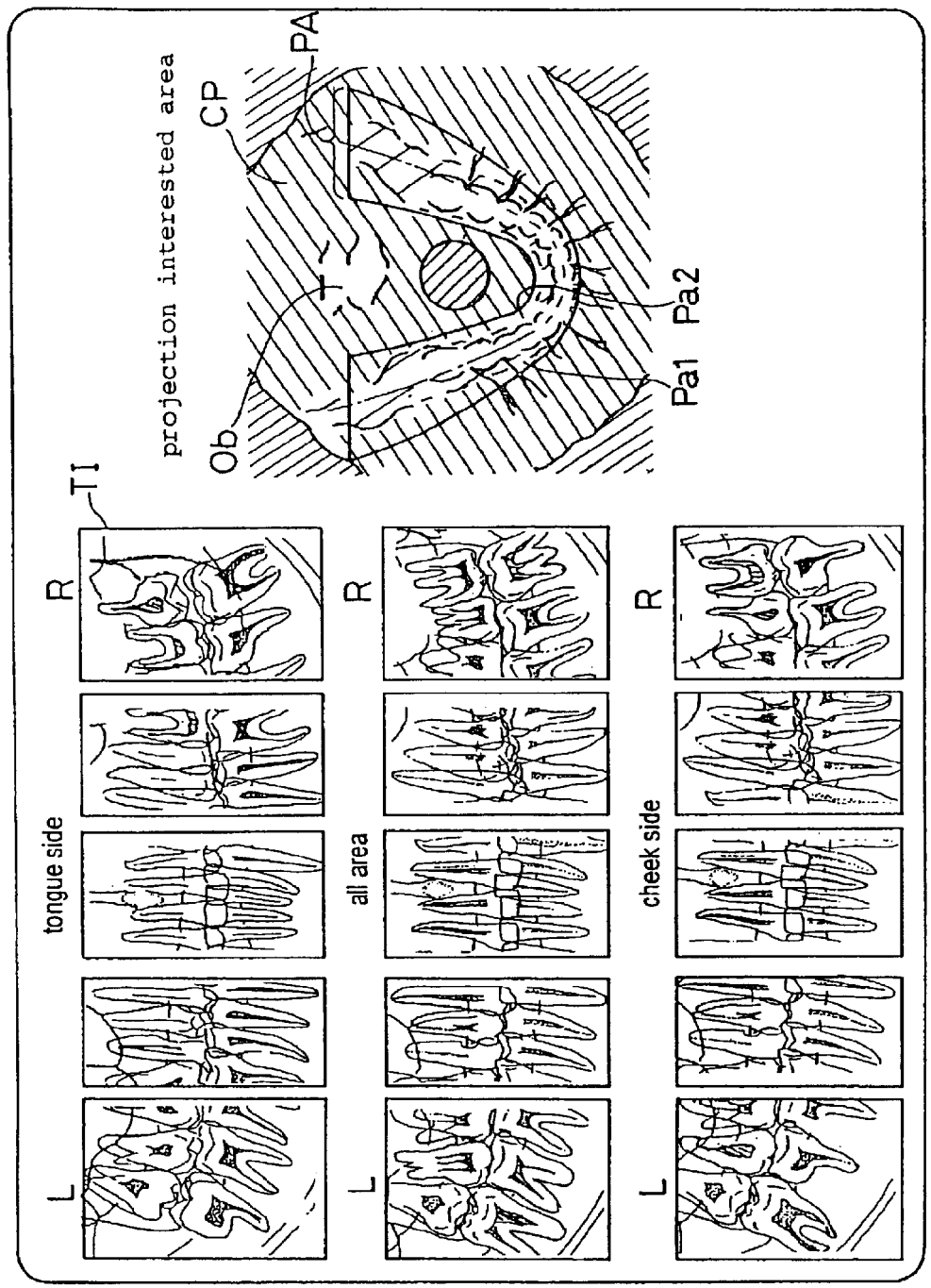
FIG. 2 is an example of displays shown by a display method of X-ray projection images for medical use according to the present invention.

FIG. 2 is an example of displays shown by a display method of X-ray projection images for medical use according to the present invention.

This figure is a display arranging showing in array the projection interested area PA explained in FIG. 1, an image of the image layer CP on which a projection interested area PA, and projection interested layers Pa1 and Pa2 are set, and an X-ray projection images TI of tongue side, entire area and cheek side produced for each part of the dental arch according to the method mentioned in FIG. 1.

The X-ray projection image TI is obtained in such a manner that a rotation center Ta of the projection plane TP is aligned with a rotation center 3a of X-ray radiation to be fixed, a tooth of which X-ray projection image is required is moved in sequence, and the projection plane TP is correspondingly rotated. When the center Ta of the projection plane TP is fixed according to radiography conditions, radiation conditions and radiography conditions are conformed so that clear X-ray projection images can be obtained and further projection procedures are simplified.

Partial tooth images of the entire dental arch S are arranged on a display in array and they can be seen contrasting the tongue side, the entire area and the cheek side, therefore treatment parts are easily specified so as to be useful for medical care. The projection interested area and the projection interested layer are shown at one time so that their corresponding relation can be easily understood. Further, if names of the selected projection interested area and the projection interested layer are also shown beside the X-ray projection images, more accurate diagnosis is possible.

Figure 3:
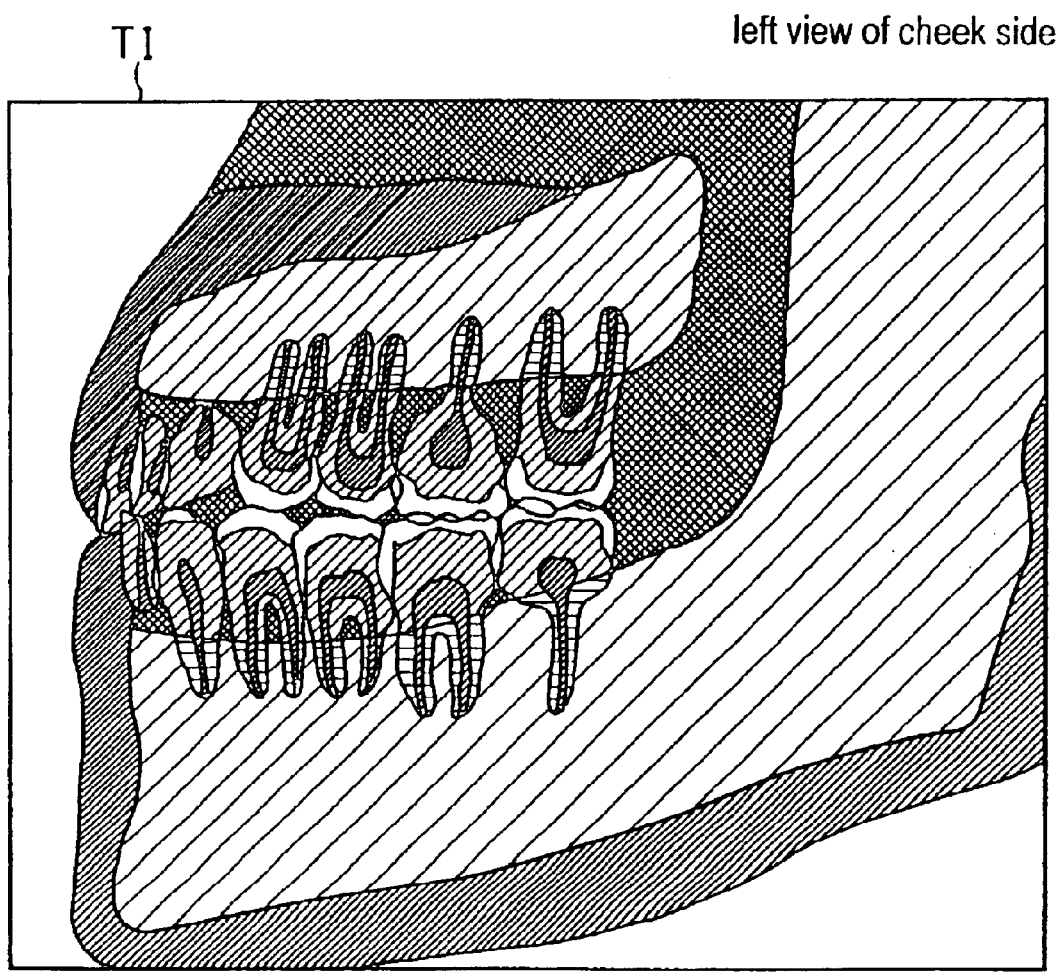
FIG. 3 is an example of X-ray projection images shown by a display method of X-ray projection images for medical use according to the present invention.
Figure 4:
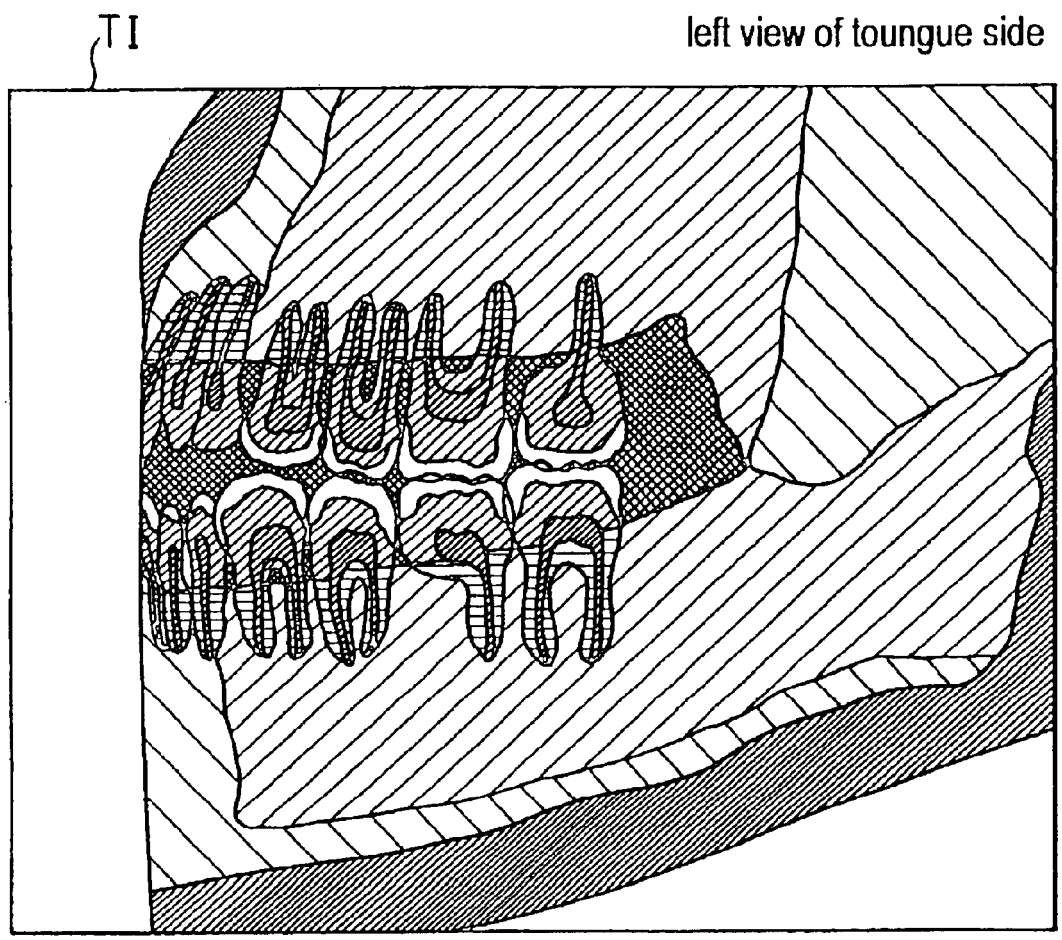
FIG. 4 is other example of X-ray projection images shown by a display method of X-ray projection images for medical use according to the present invention.
Figure 5:
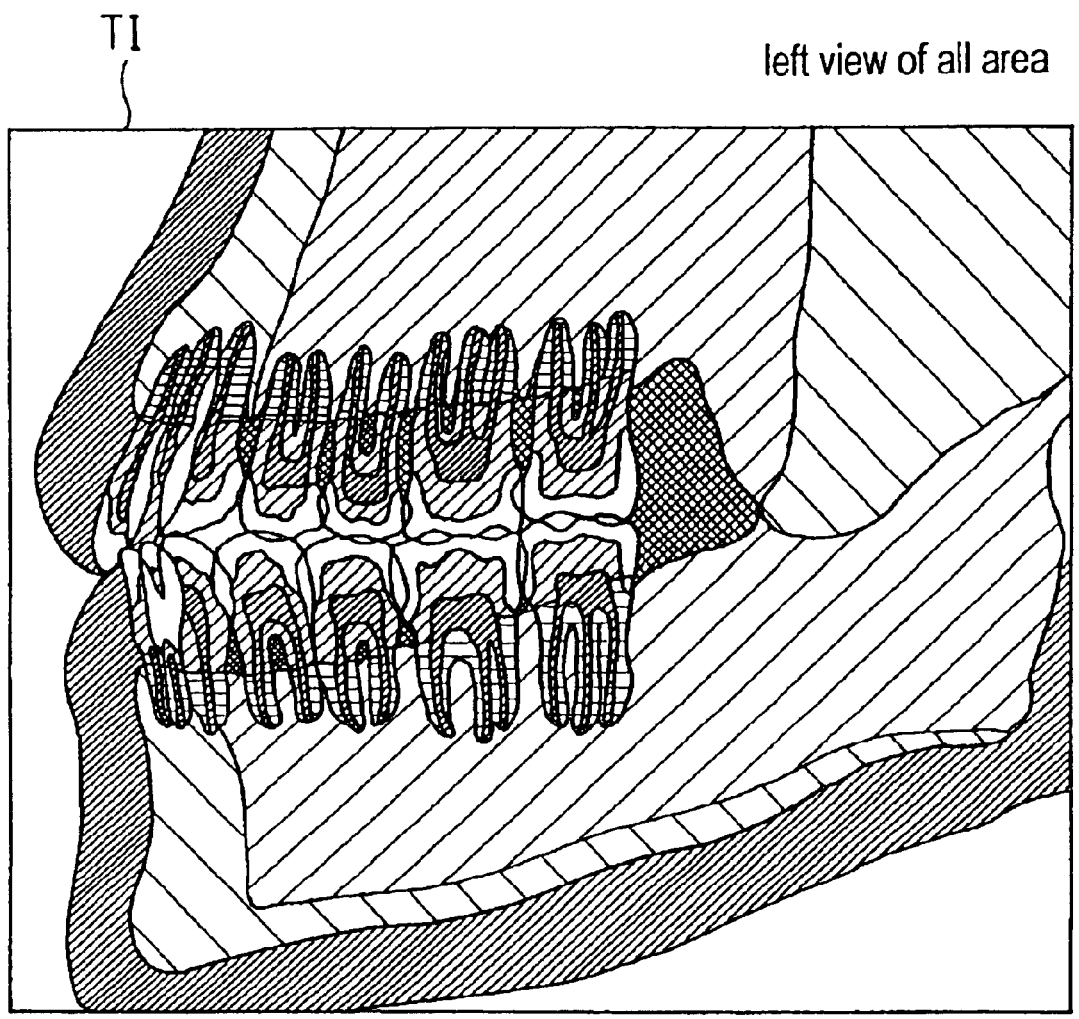
FIG. 5 is other example of X-ray projection images shown by a display method of X-ray projection images for medical use according to the present invention.
Figure 6:
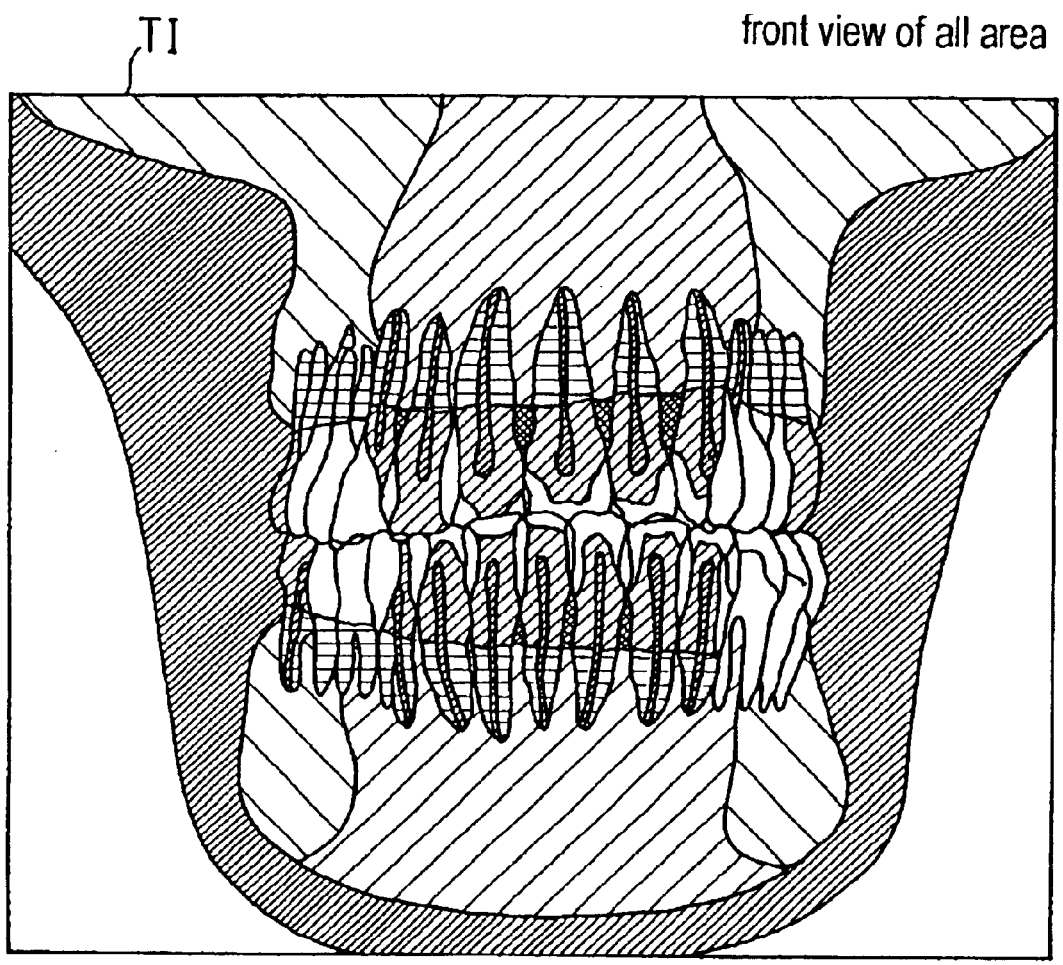
FIG. 6 is other example of X-ray projection images shown by a display method of X-ray projection images for medical use according to the present invention.
Figure 7:
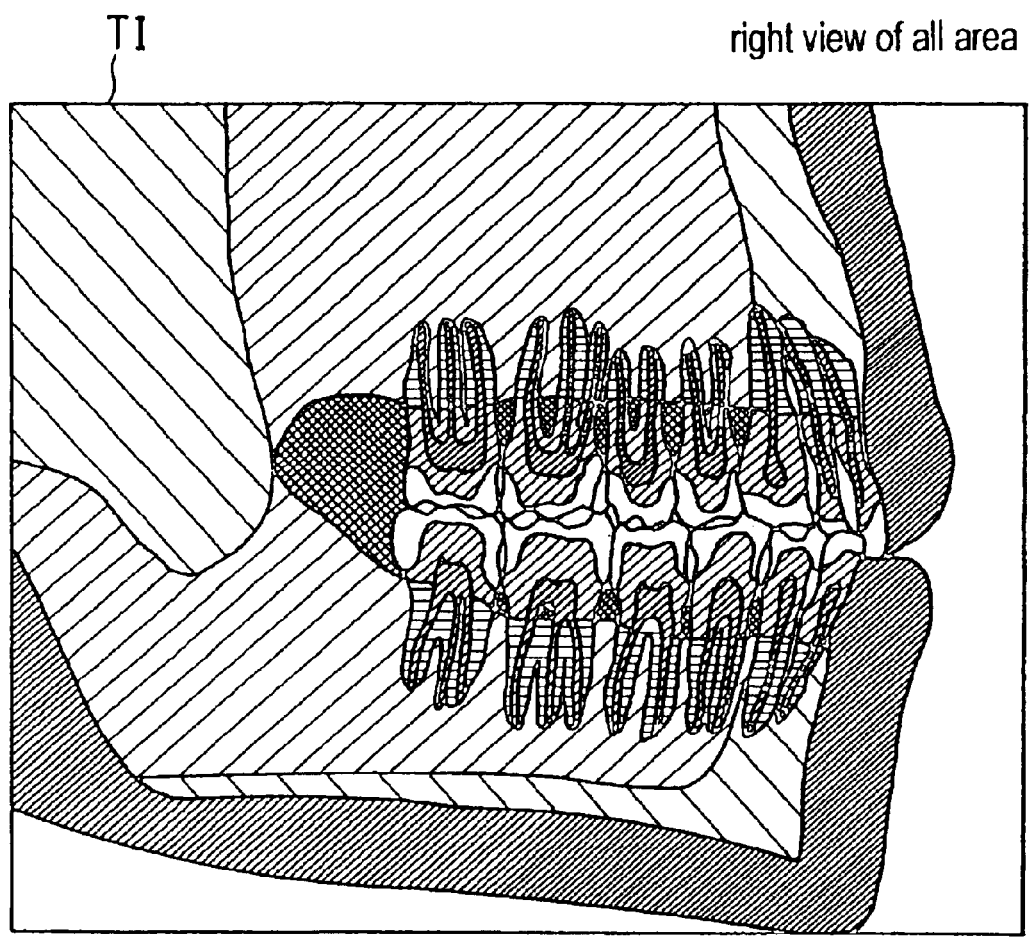
FIG. 7 is other example of X-ray projection images shown by a display method of X-ray projection images for medical use according to the present invention.

FIG. 3–FIG. 7 show an example of X-ray projection images shown by a display method of X-ray projection images for medical use according to the present invention. They are X-ray projection images constructed for broader area than the image shown in FIG. 2. FIG. 3 is an X-ray projection image TI at a cheek side when a dental arch is seen from left, FIG. 4 is an X-ray projection image TI at a tongue side seen from the same direction as FIG. 3, FIG. 5 is an X-ray projection image TI of the entire area seen from the same direction as FIG. 3, FIG. 6 is an X-ray projection image TI of the entire area when a dental arch is seen from the front and FIG. 7 is an X-ray projection image TI seen from right.

From the X-ray projection images TI in FIG. 3, FIG. 4 and FIG. 5, the dental arch S seen from a specific direction can be understood, namely a dental arch S is perspectively displayed as a normal view. Comparing with a panoramic image shown in FIG. 8, those images TI are easily understood by intuition and available for determination material for diagnosis.

Those images may be shown on a display respectively or may be shown in array like FIG. 2 such as cheek side, tongue side and entire area per each part. If they are arranged in array, each image is easily compared and the position of dental root from the cheek side to the tongue side is obtained.

From the X-ray projection images TI in FIG. 5, FIG. 6, and FIG. 7, X-ray projection images are shown by rotating the projecting direction to the dental arch, such as left, front and right. When the image of the dental arch being an object is displayed in rotation by sequentially and continuously showing plural X-ray projection images, even if a display area is limited, X-ray projection images seen from different directions can be continuously displayed, thus enabling selection of an image required for diagnosis and achieving convenience.

Specifically, in case of a dental arch, about 512 X-ray projection images taken from different projection angles are sequentially and continuously displayed at intervals from $1/30$ sec. to $1/15$ sec., thereby displaying in rotation a maxillo facial area.

Combining a display in rotation and a display in array, X-ray projection images of cheek side, tongue side and entire area are displayed in array and each X-ray projection image is displayed in rotation by sequentially changing the projecting direction.

Figure 8A:
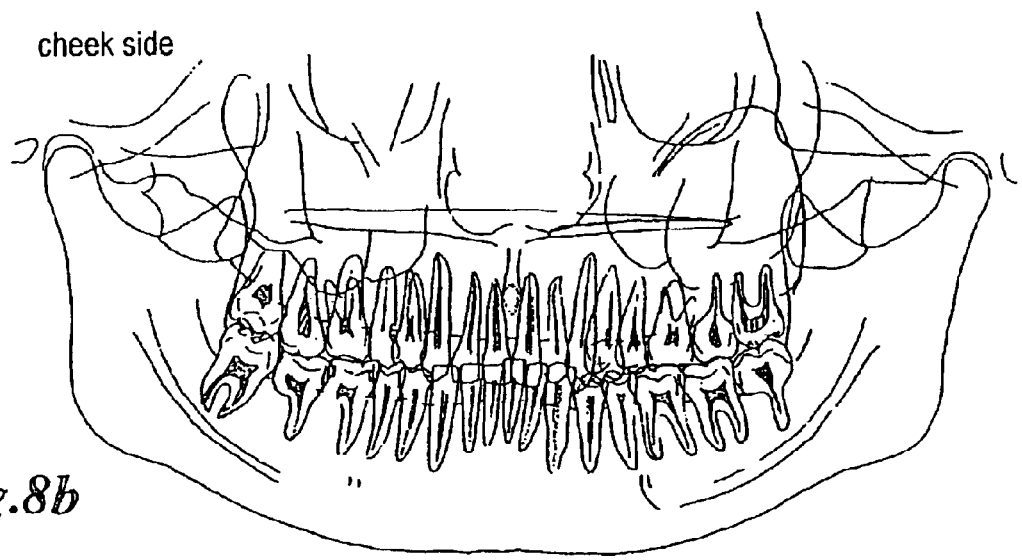
FIGS. 8a, 8b and 8c show an example of X-ray panoramic images shown by a display method of X-ray projection images for medical use according to the present invention.
Figure 8B:
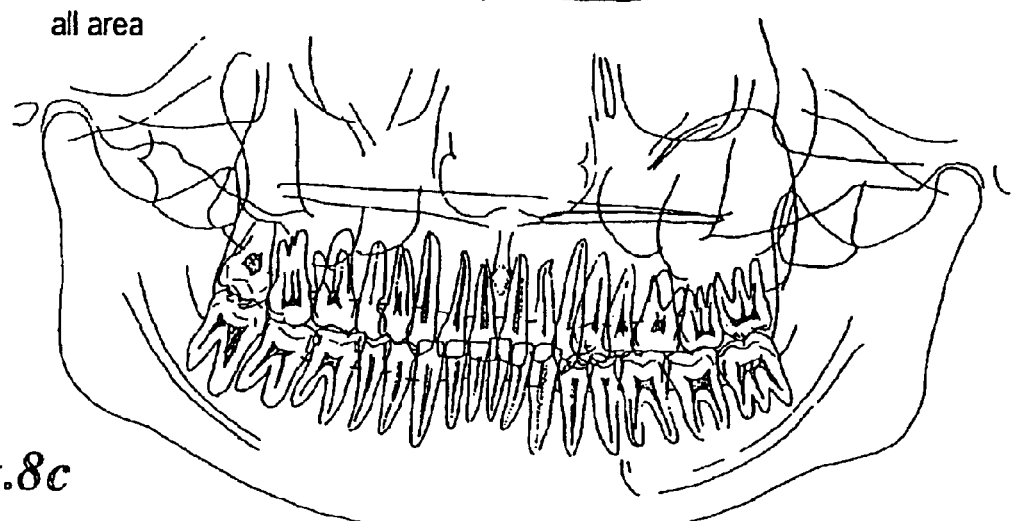
Figure 8C:
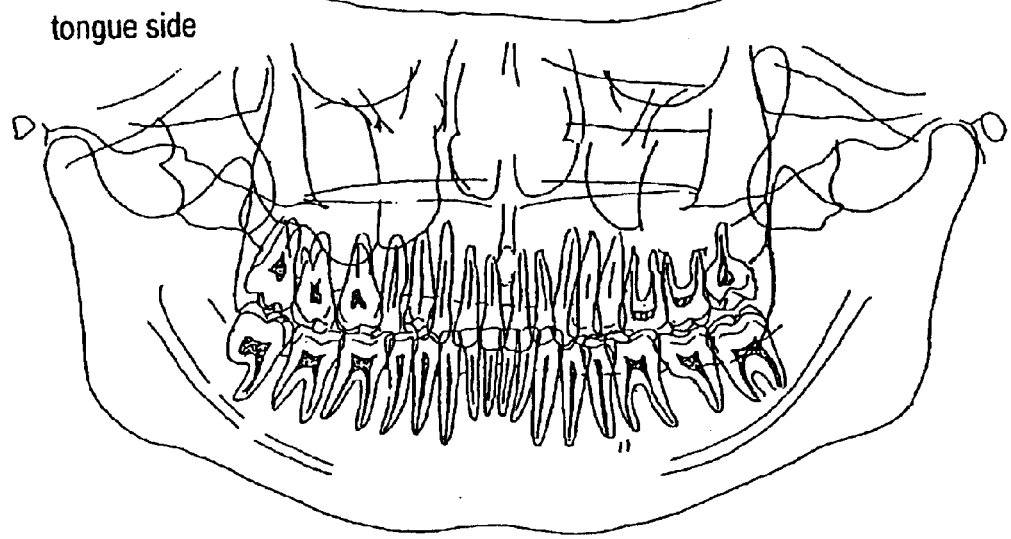

FIGS. 8a, 8b and 8c show an example of X-ray panoramic images shown by a display method of X-ray projection images for medical use according to the present invention.

Generally in case of X-ray panoramic images, a projection plane to obtain panoramic images isn't flat like the X-ray projection image in FIG. 1 but is curved and its projecting direction is as a rule perpendicular to a part of each curved projection plane. Therefore, the method of the present invention isn't applied as it is.

However, application of a projection interested area and a projection interested layer is useful for constructing X-ray panoramic images. The three dimensional X-ray absorption coefficient data to be projected on the curved projection plane in order to obtain X-ray panoramic images can be limited to those in the projection interested area or the projection interested layer.

FIGS. 8a, 8b and 8c show X-ray panoramic images V obtained by setting the projection interested area PA and the projection interested layers Pa1 and Pa2 as shown in FIG. 1 against the dental arch S. FIG. 8a is a panoramic image V at cheek side, FIG. 8b shows a panoramic image V of the entire area and FIG. 8c shows a panoramic image V at tongue side. If each name of the setting area or setting layer such as cheek side, entire area and tongue side is described beside the image, mistakes are avoided and accurate diagnosis can be executed.

As mentioned above, if the projection interested area and projection interested layer are applied to X-ray panoramic images, an image which has little obstacle shade and can show the position of a dental root from cheek side to tongue side can be obtained.

Figure 9:
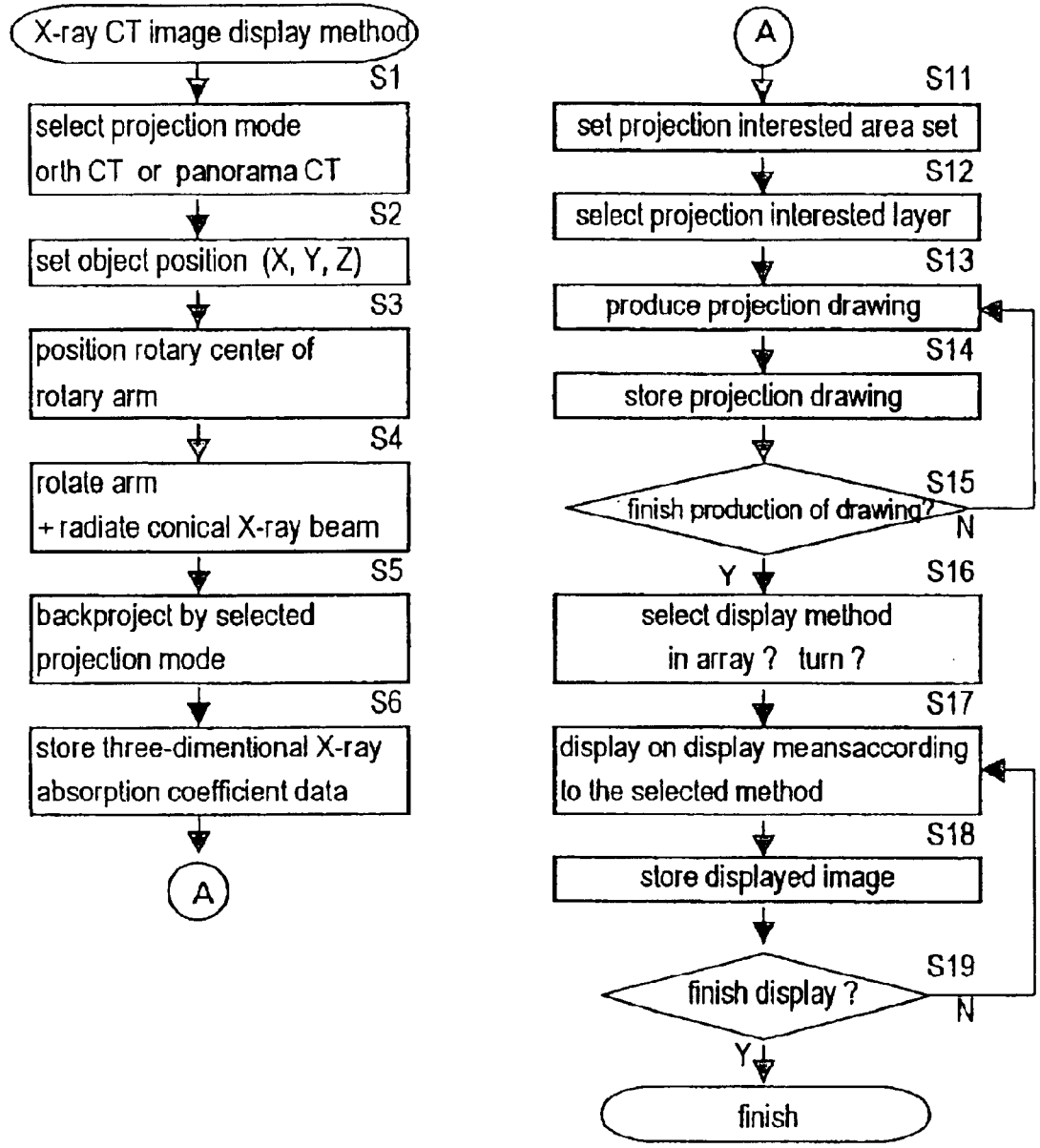
FIG. 9 is a flow chart showing one example of procedures of a display method of X-ray projection images for medical use according to the present invention.

FIG. 9 is a flow chart showing one example of procedures of a display method of X-ray projection images for medical use according to the present invention. The display procedure of the present invention will be detailed hereinafter. The procedure for obtaining three dimensional X-ray absorption coefficient data in order to apply the display method of the present invention will be explained here, however, the object of the present invention is to provide a display method and the invention isn't limited to a production method of three dimensional X-ray absorption coefficient data.

At first three dimensional X-ray absorption coefficient data are required to be obtained by radiating X-rays on an object to be examined. To this end, an imaging mode of X-ray CT is selected (S1). The reason is that this invention applies as a pre-stage a local X-ray CT method, namely a radiography in which the effects of the display method of the present invention are interactively achieved, to obtain X-ray panoramic images. In such a case, an imaging mode is required to be selected whether a general local CT mode or a CT mode for panoramic images. In this case, a panoramic CT is selected.

Figure 20:
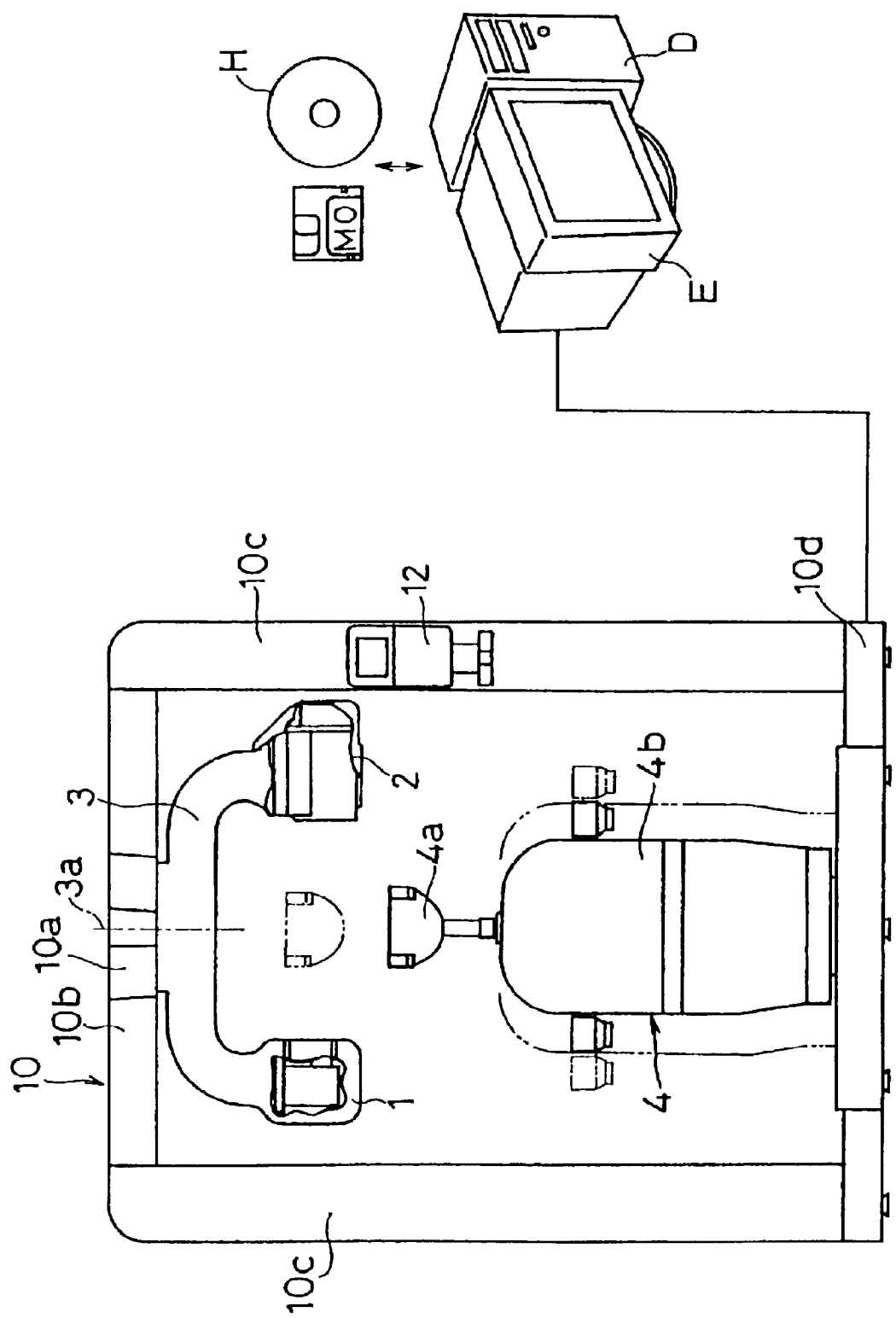
FIG. 20 is an outline view showing one example of an X-ray CT apparatus of the present invention.

Next, the object sits on a chair for picturing shown as the reference numeral 4 in FIG. 20. His head is fixed with a holding means 4a shown in FIG. 20 to set X, Y and Z positions (S2), a rotation center 3a of a rotary arm 3 in FIG. 20, namely a rotation center of X-ray radiation, is set to be a center Qa of a virtual local region Q in case of panoramic CT mode (S3).

Then conical X-ray beams are locally radiated according to a projection mode while the rotary arm is turned in a fixed angle area corresponding to a projection mode (S4), an image processing including backprojection is executed based on the obtained X-ray transmitted data according to a projection mode to obtain three dimensional X-ray absorption coefficient data (S5), and the data are stored (S6).

Thus, after obtaining three dimensional X-ray absorption coefficient data, a projection interested area PA is set as mentioned above for the obtained three dimensional X-ray absorption coefficient data (S11), a projection interested layer Pa is selected if necessary (S12), a projection plane TP from an X-ray radiating direction on a point where projection is desired is determined and a projection figure is produced by projecting three dimensional X-ray absorption coefficient data on the projection interested area PA or the projection interested layer Pa depending on the selection (S13), then the figure is stored (S14). These procedures are repeated for a desired range in the projection interested area PA (S15).

After producing and storing the projection figure, a display method is selected from a display in array, a rotary display and their combination (S16), the figures are shown on a display means according to the selected display method (S17), and the displayed images are stored if necessary (S18). These procedures are repeated in a required area and finished (S19).

According to the above-mentioned procedures, advantages of the local X-ray CT method and apparatus and three dimensional X-ray absorption coefficient data are effectively used, thereby enabling display of X-ray projection images which has little obstacle shades, is easily understandable by intuition for medical diagnosis, and can show the position of dental root from a cheek side to a tongue side.

Figure 10:
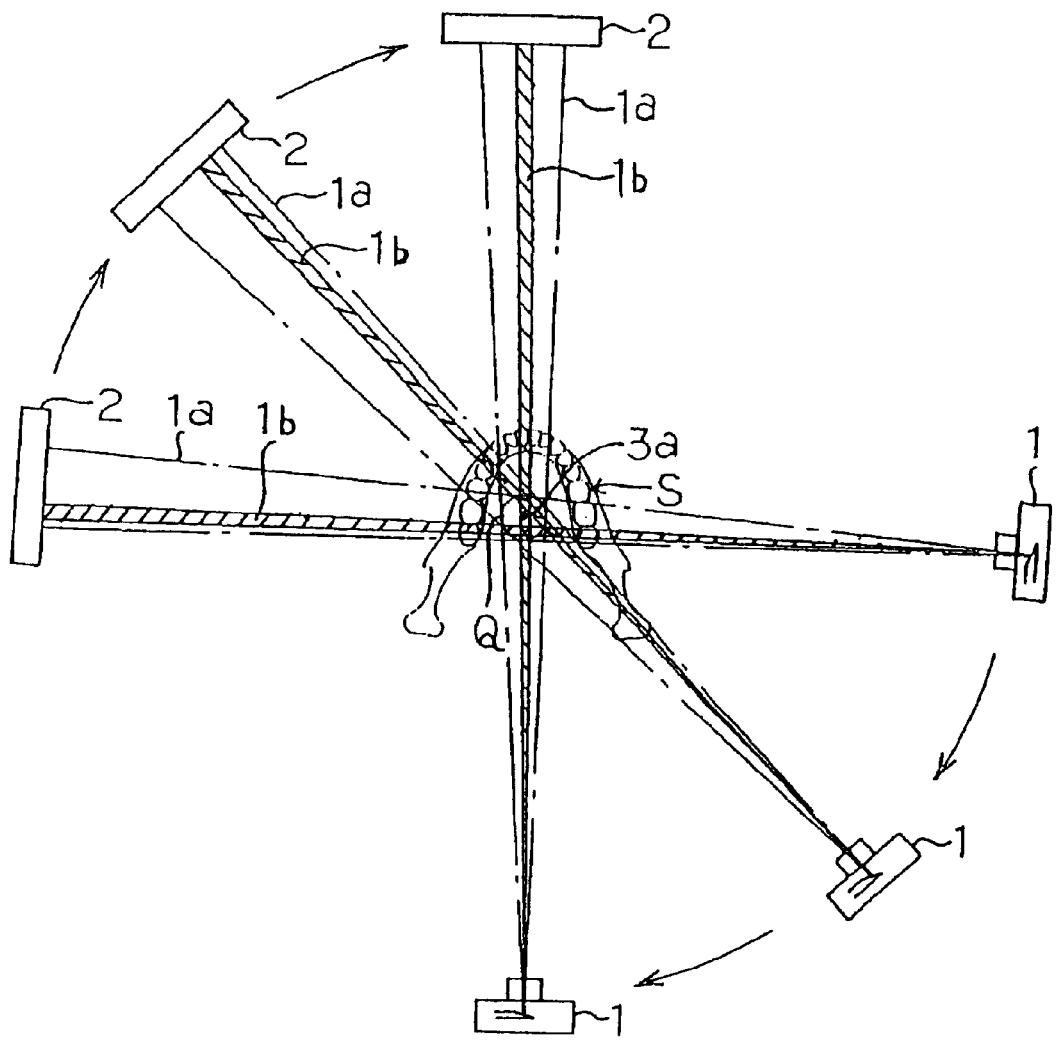
FIG. 10 is a conceptual view explaining radiography wherein a local X-ray CT method used in a display method of X-ray projection images for medical use according to the present invention is applied to panoramic images.

FIG. 10 is a conceptual view explaining a radiography method wherein a local X-ray CT method used in a display method of X-ray projection images for medical use according to the present invention is applied to panoramic images. The reference numerals already explained have the same numerals and their explanations are omitted hereinafter.

In FIG. 10, a rotary arm 3 having an X-ray generator 1 and a two dimensional X-ray image sensor 2, which is an X-ray detector, at both ends thereof is turned at a constant velocity so as to keep the width between the rotation center 3a of the rotary arm 3 and a conical X-ray beam 1a so as to form a virtual local region Q. The X-ray generator 1 radiates a conical X-ray beam 1a with a fixed width in a scanning direction accompanying with the movement of the rotary arm 3 and sequentially produces X-ray transmitted images of a dental arch S on the two dimensional X-ray image sensor 2 by the conical X-ray beam 1a. Only a partial X-ray transmitted images produced by an ortho-conical X-ray beams 1b substantially orthogonal to the dental arch S among the beam bundles of the conical X-ray beam 1a is extracted for the X-ray transmitted images sequentially produced on the two dimensional X-ray image sensor 2. The extracted partial X-ray transmitted images are arithmetically processed to obtain three dimensional X-ray absorption coefficient data of the dental arch area including the dental arch S.

Thus applying a basic local X-ray CT method wherein the rotary arm 3 is turned with its center 3a fixed during radiation and a conical X-ray beam 1a with a predetermined width is locally radiated, three dimensional X-ray absorption coefficient data for X-ray panoramic images can be produced. Further, the X-ray exposure duration is short and the exposed dose amount is reduced into 1/50 of the prior CT method, in addition a sufficient three dimensional X-ray absorption coefficient data can be obtained like the prior art.

Figure 11:
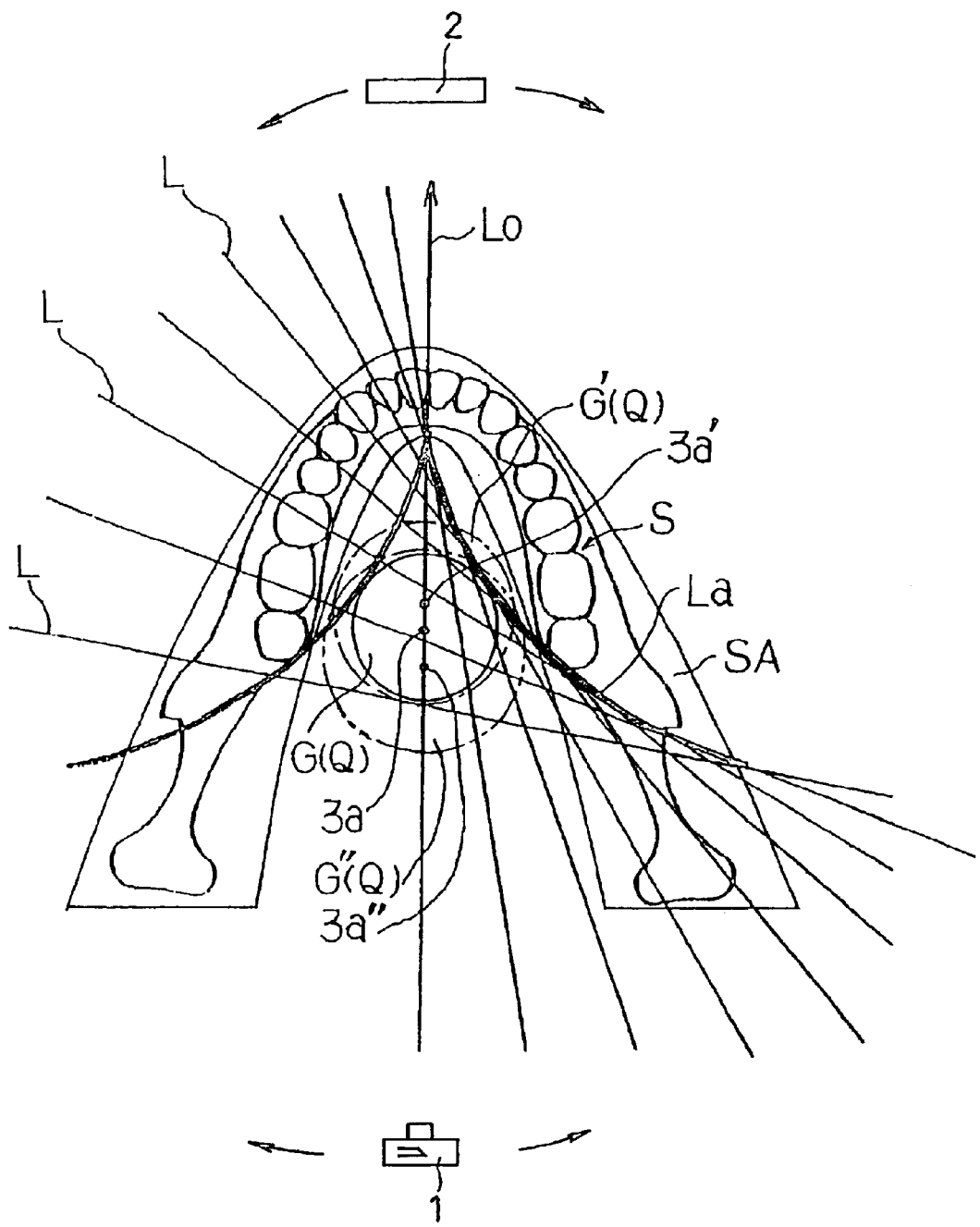
FIG. 11 is a conceptual diagram explaining one example of setting methods of a rotation center of a rotary arm when a local X-ray CT method is applied to panoramic images.

FIG. 11 is a conceptual diagram explaining one example of setting methods of a rotation center of a rotary arm when a local X-ray CT method is applied for panoramic images.

According to a local X-ray CT method, the rotation center 3a of the rotary arm 3 is aligned with the center of a virtual local region on an axis of symmetry Lo at the center of the dental arch area SA, the rotary arm is turned at a constant velocity or a variable speed in a rotary angle area according to radiography conditions, and a conical X-ray beam with a fixed width is locally radiated, thus obtained X-ray transmitted images of the dental arch area SA.

Generally in case of prior film-type panoramic imaging, it is required to execute radiography while an X-ray beam bundle is moved by transferring the rotation center of the rotary arm in such a manner that X-rays become orthogonal to the dental arch for each tooth in the curved sectional area SA. In FIG. 11, such X-ray beam bundle is shown with the reference numeral L. When X-ray beam bundles L . . . substantially orthogonal to each tooth are shown for the dental arch area SA, an envelope line La of each X-ray beam bundle L . . . is produced. Assuming an incircle G which touches internally the envelope line La, all the X-ray beams for the dental arch area SA passes through the incircle G.

In this local X-ray CT, a center Ga of the incircle G is aligned with the center 3a of the rotary arm 3 and radiation is executed by turning the rotary arm without moving the rotation center 3a thereof. Conical X-ray beam 1a with a fixed width so as to include the incircle G is locally radiated on the object from its surround. The conical X-ray beam 1a always includes X-ray beam bundles substantially orthogonal to the dental arch area SA (called as an ortho-conical X-ray beam hereinafter).

In this example, the incircle G becomes a virtual local region as shown in FIG. 10, which is also referred to the reference numeral Q. The X-ray beam bundles orthogonal to each tooth are the ortho-conical X-ray beams as mentioned above, which are shown as the reference numeral 1b.

When the X-ray conical beam 1a is locally radiated so as to form the virtual local region Q, partial X-ray transmitted images obtained by the ortho-conical X-ray beams 1b substantially orthogonal to the dental arch area SA are extracted from the X-ray transmitted images of the dental arch area SA sequentially produced on the two dimensional X-ray image sensor 2 and are arithmetically processed to obtain the three dimensional X-ray absorption coefficient data of the dental arch area SA.

A projection method wherein the local X-ray CT method used in the X-ray CT apparatus of the present invention is applied to panoramic images is based on the above-mentioned concept. The position of the rotation center 3a of the rotary arm 3 and the width of the conical X-ray beam 1a, namely the position and size of the specific region Q, are appropriately set according to the images to be produced finally. In summary, ortho-conical X-ray beams according to the images are necessary to be included in conical X-ray beams.

For example, the center 3a of the rotation center 3 which is set at the same time of radiation and the width of conical X-ray beam, that is the virtual local region Q, aren't limited to the above-mentioned incircle G internally touching the envelope line La. It may be an incircle G' or G" shown in FIG. 11. If such a circle is defined as the region Q, the center of the circle is always on the axis of symmetry Lo inside of the dental arch S. The position of the center 3a of the rotary arm 3 when the region Q is the incircle G' or G" is shown as the reference numerals 3a' or 3a".

X-ray panoramic images are not limited to ortho-radial X-ray panoramic images in which X-ray beam bundles are substantially orthogonal to the tooth. There are standard X-ray panoramic images, X-ray panoramic images of a jawbone and X-ray panoramic images on either one side of right or left. In such images, ortho-conical X-ray beams aren't always orthogonal to the dental arch S. If X-ray panoramic images by such a radiography method are produced, the position of the center 3a of the rotary arm 3 on the axis of symmetry Lo of the dental arch S and the width of conical X-ray beam 1a, namely the local region Q, are required to be determined so as to include all the ortho-conical X-ray beams 1b. Such examples are the above-mentioned incircles G' and G". For producing X-ray panoramic images on either side of right or left, the center 3a of the rotary arm 3 may be inside of the dental arch area SA or may not be on the axis of symmetry Lo.

The local region Q to produce the X-ray panoramic images is determined corresponding to the X-ray panoramic images to be produced. Smaller area is better considering the reduction of the X-ray exposure amount.

As understood from FIG. 11, the rotary arm 3 is required to be turned over 180 degrees, however it isn't required to be turned 360 degrees. Namely radiation is executed by turning the rotary arm 3 from 180 degree to 360 degree. If the angle is small, the X-ray exposed dose can be reduced accordingly.

In this invention an improved radiography method when the local X-ray CT method is applied to panoramic images is also proposed such that the rotation center 3a is moved by the minute during X-ray radiation without fixing the center 3a. For example, the center 3a may be moved along an envelope line La like a film-type radiography.

In such a case, while keeping the effect of reduction of the local X-ray exposed amount and the effect of reduction of imaging time which are characteristic of the local X-ray CT, only more narrow ortho-conical X-ray beams are radiated although a movement control of the rotary arm 3 becomes complicated. Further, a radiated tooth is disposed near the rotation center so that transmitted images with a constant size can be always radiated on the X-ray detector 2. Therefore, the detector area is effectively used, images with constant resolution and accuracy can be obtained. This method is also generally used other than panoramic images.

When the rotation center 3a is moved during X-ray radiation, the rotation center Ta of the projection plane TP is correspondingly moved as explained referring to FIG. 1, then the projection conditions conform with the radiation conditions to obtain clearer X-ray projection images.

Further, if an X-ray tube voltage and/or an X-ray tube current are changed during X-ray radiation, or if X-rays are radiated while varying the rotation speed of the rotary arm 3, density compensation depending on the radiated tooth can be executed, thus obtaining better X-ray projection images.

Figure 12:
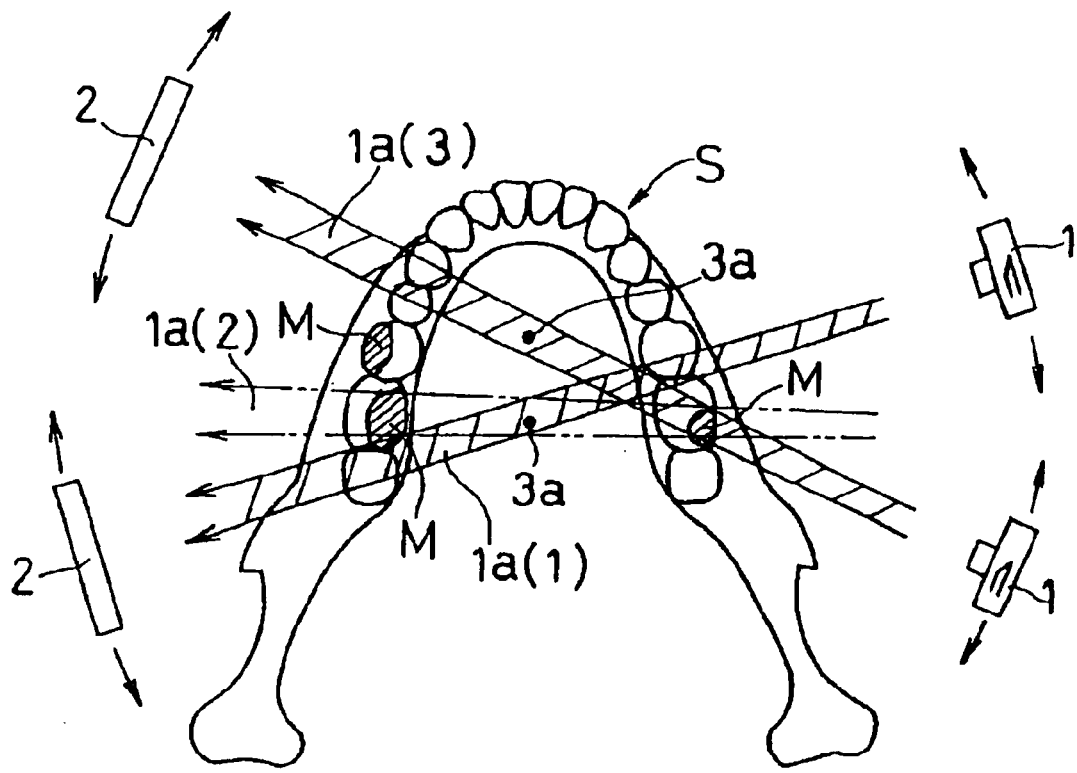
FIG. 12 is a conceptual diagram explaining other example of setting methods of a rotation center of a rotary arm when a local X-ray CT method is applied to panoramic images.

FIG. 12 is a conceptual diagram explaining other example of setting methods of a rotation center of a rotary arm when a local X-ray CT method is applied to panoramic images.

In this embodiment, there exists metal M such as crown at plural teeth. If X-rays are radiated from the conical X-ray beam 1a(1) to 1a(2) while fixing the center 3a of the conical X-ray beam 1a, X-rays are radiated on both metals M of a forward teeth and of a rear teeth at the conical X-ray beam 1a(2). In such a case a metal artifact is generated so that correct X-ray transmitted images can't be obtained and hence correct three dimensional X-ray absorption coefficient data can't be obtained.

In order to avoid such simultaneous radiation on plural metals M, X-rays are radiated by moving the rotation center 3a in such a manner that the conical X-ray beam 1a is positioned like 1a(3) after 1a(1).

The effect of moving the rotation center 3a is to avoid the metal artifact as mentioned above, thereby obtaining better three dimensional X-ray absorption coefficient data and better X-ray projection images.

Figure 13A:
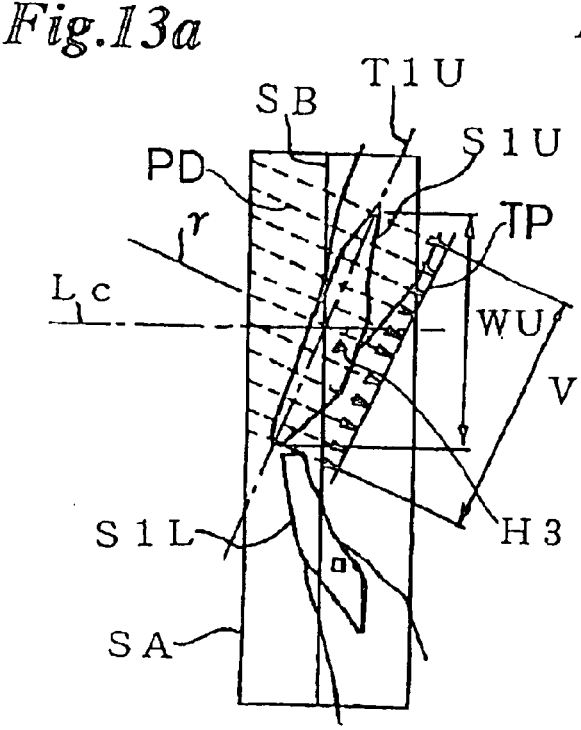
FIGS. 13a and 13b are conceptual diagrams showing one example of X-ray radiation method of X-ray CT used by an X-ray CT apparatus for medical use according to the present invention.
Figure 13B:
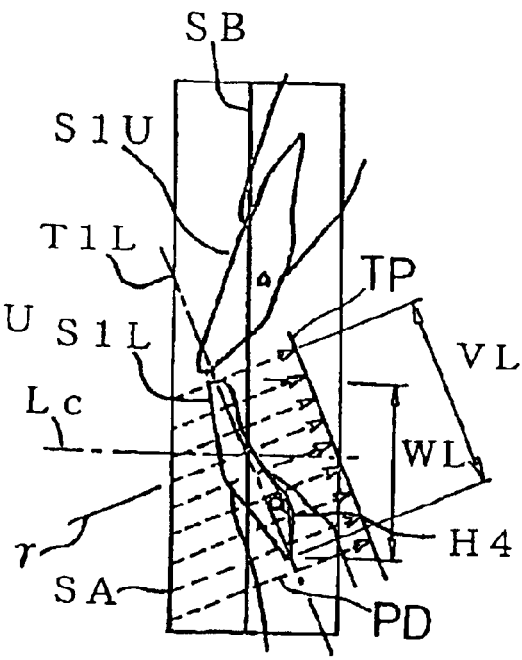
Figure 13C:
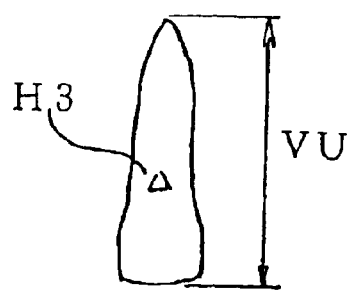
FIGS. 13c and 13d show one example of X-ray projection images obtained by the method.
Figure 13E:
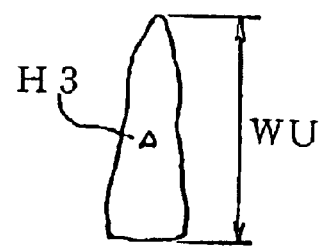
FIGS. 13e and 13f show one example of X-ray projection images obtained by a prior art.
Figure 13D:
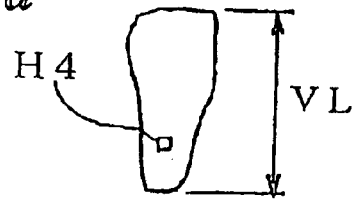
Figure 13F:
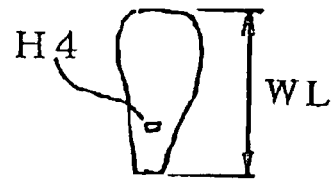
Figure 14A:
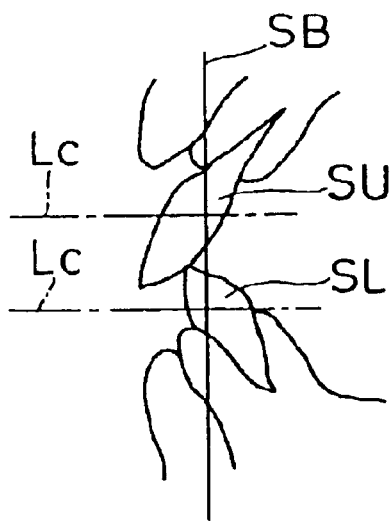
FIG. 14a is a conceptual diagram when the teeth are seen from a direction of a general normal line.
Figure 14B:
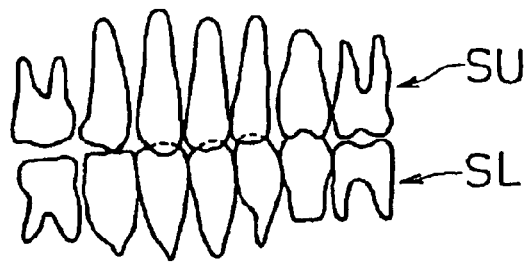
FIG. 14b shows thus obtained X-ray projection image.
Figure 14C:
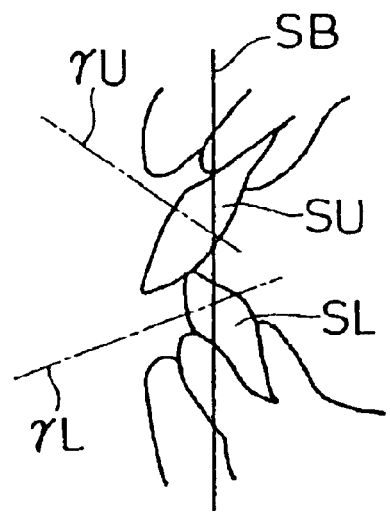
FIG. 14c is a conceptual diagram when the teeth are seen from a normal line into a rising direction of the teeth.
Figure 14D:
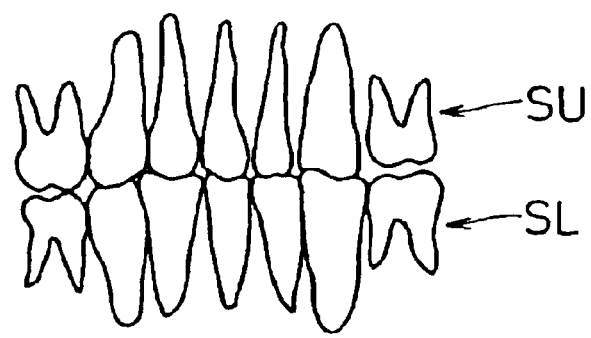
FIG. 14d shows thus obtained X-ray projection image.

FIGS. 13a and 13b are conceptual diagrams showing one example of X-ray radiation method in an X-ray CT used for an X-ray CT apparatus for medical use according to the present invention. FIGS. 13c and 13d show one example of X-ray projection images obtained by the method. FIGS. 13e and 13f show one example of X-ray projection images obtained by a prior art.

FIG. 13a shows the dental arch area SA in a form of a vertical section of a front jaw. In the figure, an upper front tooth S1U and a lower front tooth S1L are shown. FIGS. 13a, 13c and 13e show the upper front tooth S1U and FIGS. 13b, 13d and 13f show the lower front tooth S1L.

In this method, X-rays are radiated on a normal line γ against a rising direction T1U of the upper front tooth S1U. The projection plane TP perpendicular to the normal line γ is determined and three dimensional X-ray absorption coefficient data on the dental arch area SA which is also a projection interested area are projected on the plane TP, thus obtaining X-ray projection images.

This method is applied to the lower front tooth S1L in the same manner. The reference numeral T1L in the figure shows a rising direction of the lower front tooth S1L. The length of the upper front tooth S1U and the lower front tooth S1L in a direction of a panoramic sectional area SB of the dental arch S is shown as WU and WL respectively, and the length perpendicular to the nominal line γ is shown as VU and VL respectively. The reference numerals H3 and H4 show a foreign material hidden in the upper front tooth S1U and in the lower front tooth S1L.

FIG. 13c is a partial view of the upper front tooth S1U of the produced X-ray projection image TI and FIG. 13d is a partial view of the lower front tooth S1L. FIGS. 13e and 13f show partial views of the X-ray projection image TI projected on a projection plane TP including a central perpendicular line SB of the dental arch area SA regardless a rising direction.

Comparing those figures, it is understood that the length VU and VL which is an actual entire length of the upper front tooth S1U and the lower front tooth S1L and an accurate position of the foreign material H3 and H4 for the length VU and VL are obtained by FIGS. 13c and 13d. The lengths WU and WL obtained by FIGS. 13e and 13f were varied by the angle of a rising direction T1U and T1L of the upper front tooth S1U and the lower front tooth S1L, therefore accurate length were not obtained.

According to this method, the X-ray projection images in which each tooth is clearly appeared, not the X-ray projection images parallel to the central perpendicular line SB of the dental arch SA, can be obtained.

The normal line γ is changed as the rising direction is varied according to the tooth and is determined corresponding to each tooth.

In FIG. 14 the X-ray radiation method in FIG. 13 is applied to other teeth. FIG. 14a is a conceptual diagram when the teeth are seen from a direction of a general normal line, FIG. 14b shows thus obtained X-ray projection image, FIG. 14c is a conceptual diagram when the teeth are seen from a normal line into a rising direction of the teeth, and FIG. 14d shows thus obtained X-ray projection image.

Comparing each figure in FIG. 14, X-rays are radiated in such a manner that an upper X-ray radiating direction, a projecting direction γU, and a lower X-ray radiating direction, a projecting direction γL become a nominal line direction into a rising direction of the upper tooth SU and the lower tooth SL respectively. X-ray projection images are produced based on thus obtained three dimensional X-ray absorption coefficient data, the length of each tooth is shown in approximately the same as an actual size and if the upper tooth and the lower tooth are overlapped, the overlapped part is eliminated on the image, achieving convenience for diagnosis. Otherwise, a radiography is executed from a direction orthogonal to a rotation axis of X-ray radiation and the X-ray projection image is shown by setting a projection plane parallel to an inclination of the tooth only for display.

Figure 15A:
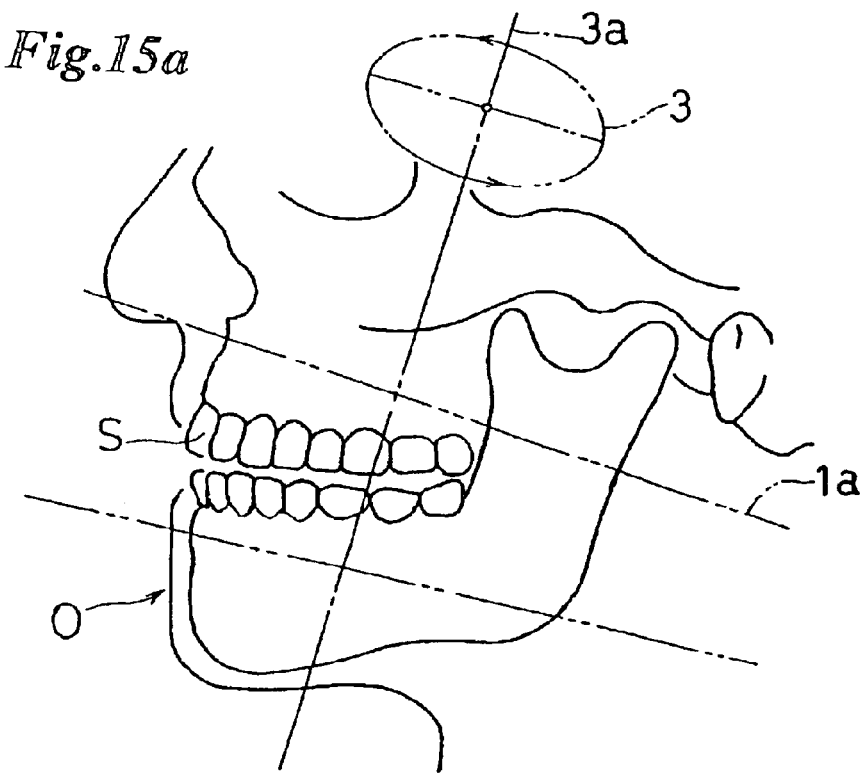
FIGS. 15a and 15b are conceptual diagrams showing other example of an X-ray radiation method in an X-ray CT used in an X-ray CT apparatus for medical use according to the present invention.
Figure 15B:
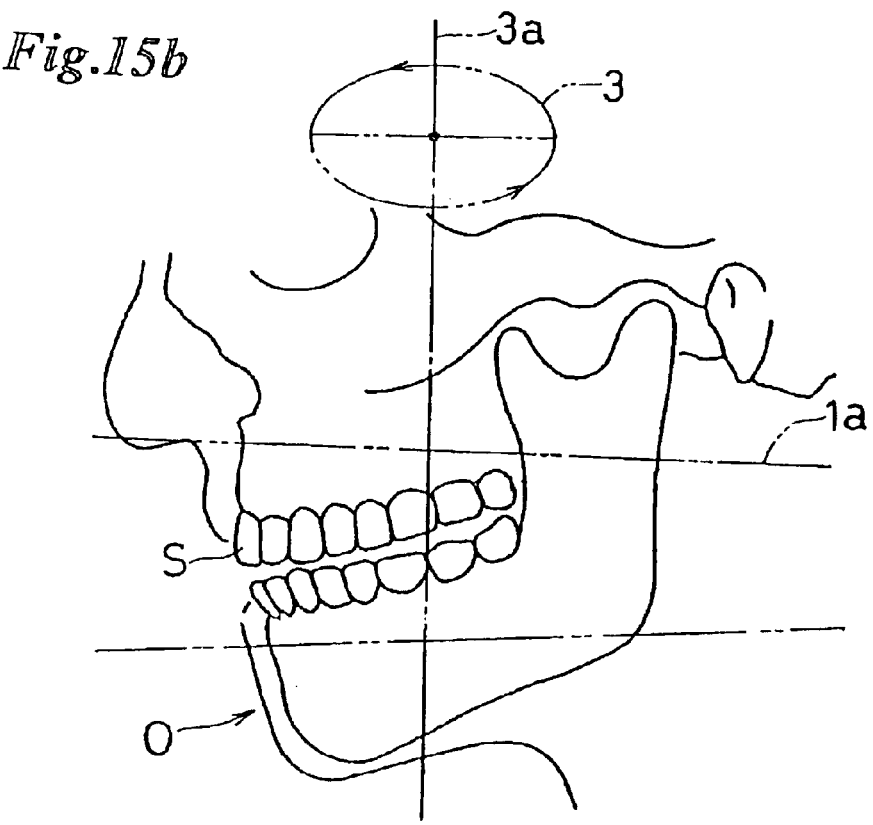

FIGS. 15a and 15b are conceptual diagrams showing other example of X-ray radiation method in an X-ray CT method used for an X-ray CT apparatus for medical use according to the present invention.

As seen from the figures, if a rotation center 3a of the rotary arm 3, namely an axial direction of the rotation axis, is inclined for the object O like FIG. 15a, or if the object O is inclined for the axial direction of the rotation axis 3a of the rotary arm 3 which is a vertical direction, affect of obstacle shadows such as a jawbone is eliminated. In case of FIG. 15b, the object O which doesn't rotate is inclined so that the construction of an object holding means (described later) which is an inclination means is simplified.

Thus the radiating direction is inclined, for projecting the obtained three dimensional X-ray absorption coefficient data, the projecting direction is aligned with the inclined direction, obtaining clearer X-ray projection images.

The flat plane perpendicular to the rotation center 3a and produced by radiating and rotating conical X-ray beams 1a as a central axis of the rotation center 3a is called as a radiation plane.

Figure 16:
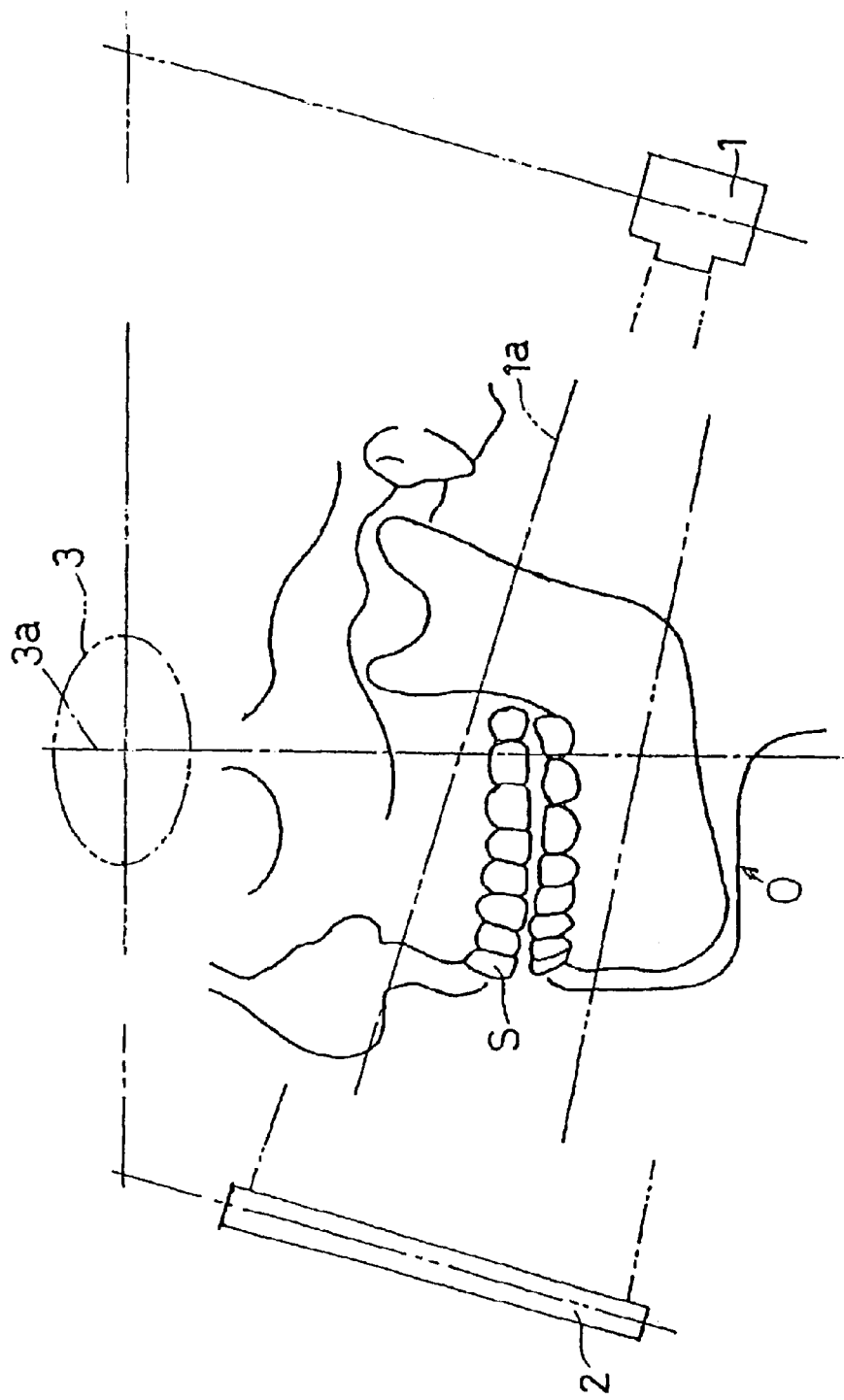
FIG. 16 shows a conceptual diagram showing other example of an X-ray radiation method in an X-ray CT used in an X-ray CT apparatus for medical use according to the present invention.

FIG. 16 shows a conceptual diagram showing other example of X-ray radiation method in an X-ray CT used in an X-ray CT apparatus for medical use according to the present invention.

As a method for inclining a radiating direction, other than inclining the axial direction of the rotation center 3a and inclining the object, the X-ray generator 1 and the X-ray detector 2 are inclined against the rotary arm 3 as shown in this figure. The same effect as mentioned above can be achieved.

Figure 17:
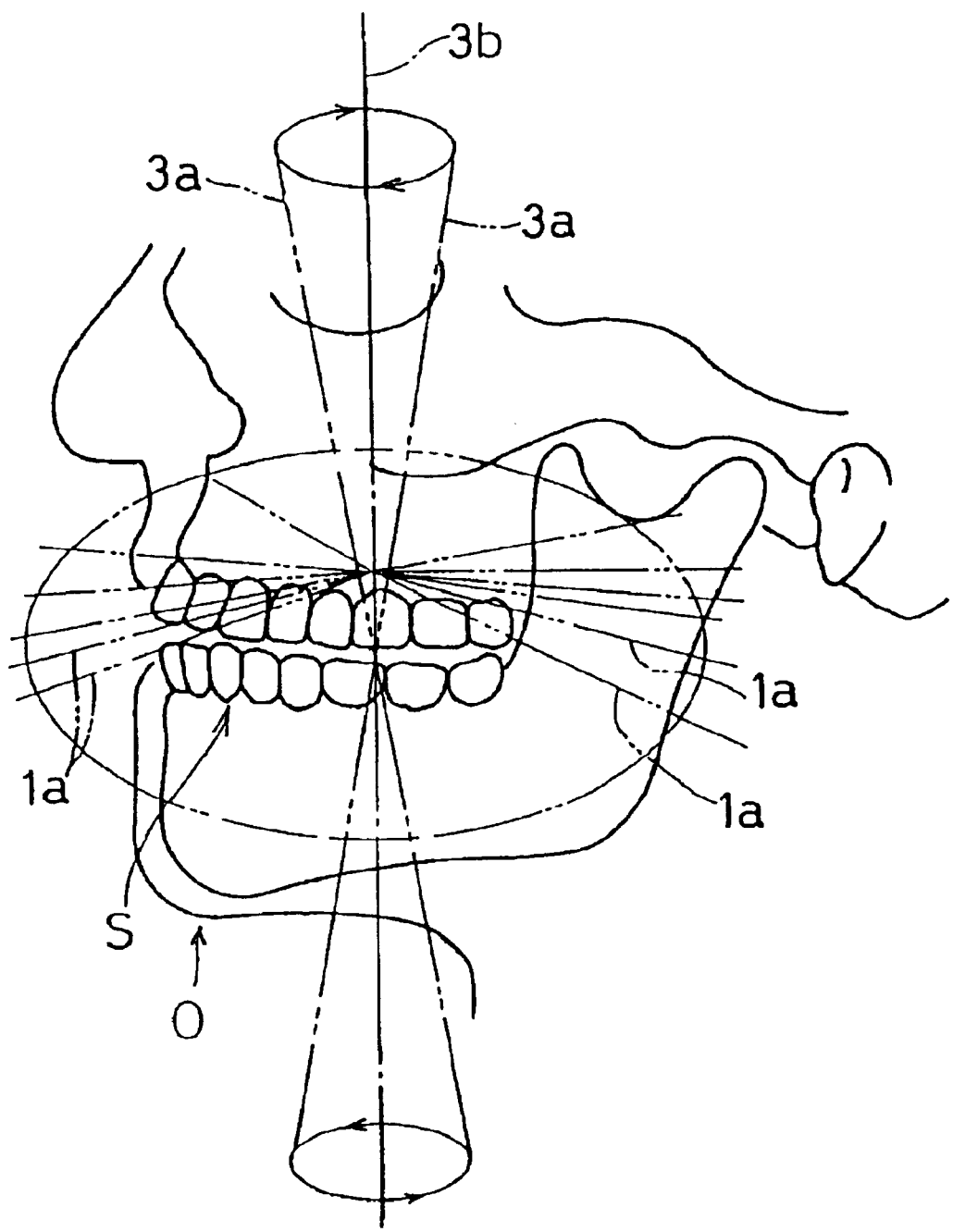
FIG. 17 shows a conceptual diagram showing other example of an X-ray radiation method in an X-ray CT used in an X-ray CT apparatus for medical use according to the present invention.

FIG. 17 shows a conceptual diagram showing other example of X-ray radiation method in an X-ray CT used in an X-ray CT apparatus for medical use according to the present invention. In this method a rotation axis of a rotary arm executes precession.

As seen from FIG. 17 while the rotation axis, the rotation center 3a of the rotary arm 3 executes precession, namely a grinding operation in such a manner that the center 3a is rotated around a specific point against a specific rotation axis 3b keeping a predetermined angle into a direction shown as an arrow, conical X-ray beams 1a are radiated by turning the rotary arm 3. Comparing with a vertical radiation or with a case a rotation axis is simply inclined, alternatives of a projection method of X-ray conical beams 1a so as to avoid obstacle shades are increased so that the method can more suitably correspond to several kinds of obstacle shades.

In case of X-ray panoramic radiography, not a normal CT, X-rays are radiated with about 5 degrees of angle of elevation in order to alleviate the obstacle shades. Executing the same method for CT, X-ray transmitted images with less obstacle shades can be obtained and three dimensional X-ray absorption coefficient data with less obstacle shades can be obtained by backprojection based on the X-ray transmitted images.

Also in this case, when the projecting direction is aligned with the radiating direction executing precession, better X-ray projection images can be obtained.

Figure 18:
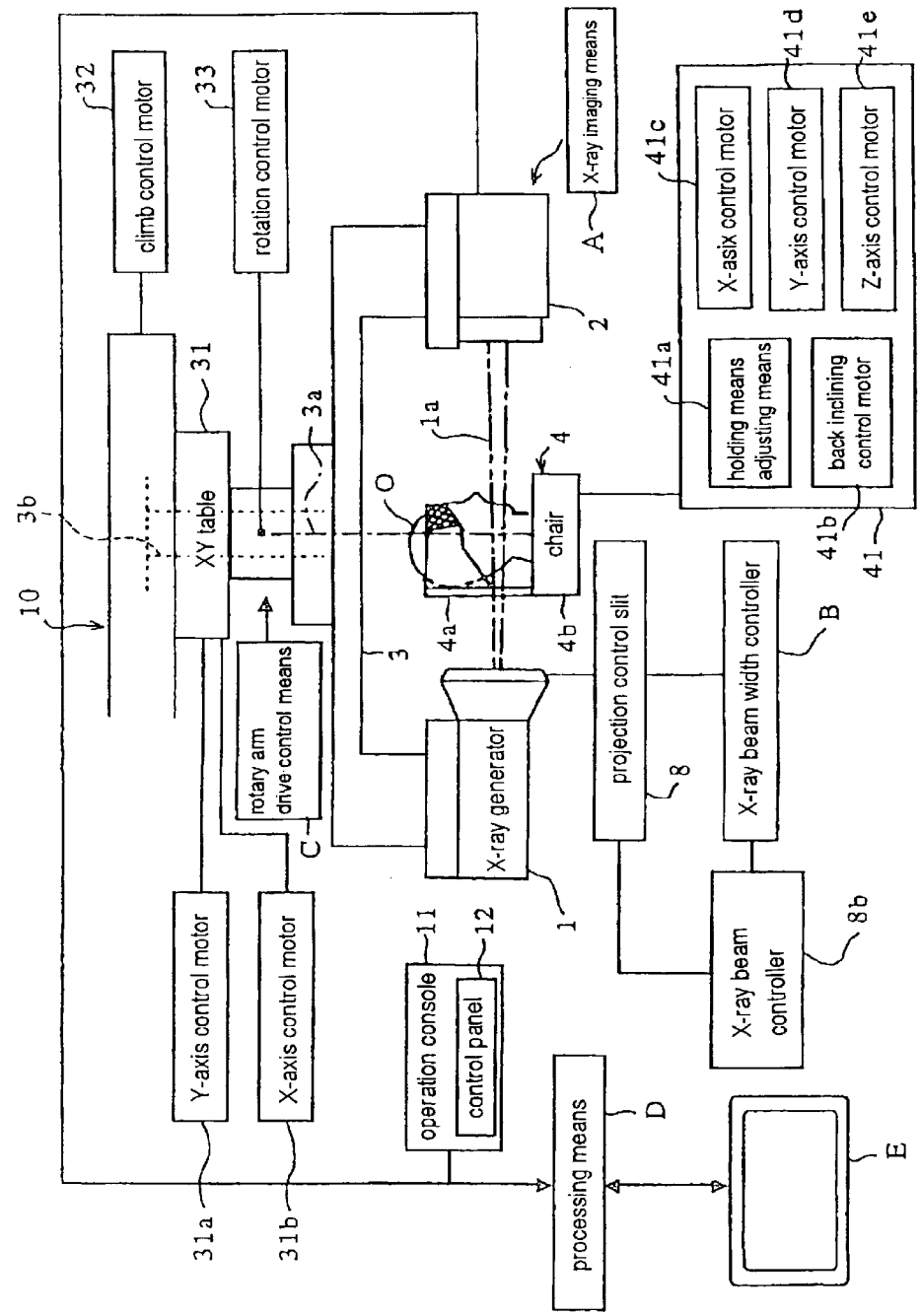
FIG. 18 shows a basic construction of one example of an X-ray CT apparatus according to the present invention.

FIG. 18 shows a basic construction of one example of an X-ray CT apparatus according to the present invention.

X-ray CT apparatus 20 in FIG. 18 is provided with an X-ray imaging means A, an X-ray beam width restriction means B, a rotary arm driving control means C, an arithmetic processing means D, a display means E, an object holding means 4, a main frame 10, an operation console 11 and an operation panel 12.

The X-ray imaging means A has a rotary arm 3 from which an X-ray generator 1 and a two dimensional image sensor 2 opposing each other are suspended.

The X-ray generator 1 has an X-ray beam width restriction means B with a radiation control slit 8 and an X-ray beam controller 8b in such a manner that X-ray beams radiated from an X-ray tube are controlled by the X-ray beam width restriction means B so as to emit conical X-ray beams 1a or ortho-conical X-ray beams 1b with a desired width.

The two dimensional X-ray image sensor 2 is a well known type in which an X-ray image intensifier II, in short X-ray II, and a CCD camera are combined. In this sensor, the X-rays run into a scintillator layer provided on the surface of the X-ray II is converted into a visible light and the visible light is converted into electron to be electrically intensified by a photoelectric converter and the electron is converted to a visible light by a fluorescent material to be pictured by a two dimensionally arranged CCD camera (solid-state image sensing device) through a lens.

Otherwise, as an image sensor, a two dimensional X-ray image sensor such as a cadmium telluride detector and a MOS sensor, and a well known two dimensional X-ray image sensor such as a CCD image sensor which is a combination of a scintillator, a glass fiber, and the CCD may be used.

An XY table 31, an elevation control motor 32, a rotation control motor 33 are provided for the rotary arm 3. The rotation center 3a is adjustable in an X-Y direction by controlling an X-axis control motor 31a and a Y-axis control motor 31b and is adjustable vertically by driving the elevation control motor 32. Further for imaging, the rotation control motor 33 is driven at a constant velocity so as to turn the rotary arm 3 about the object O. The elevation control motor 32 constitutes a vertical arm position control means of the rotary arm 3.

The center 3a of the rotary arm 3, namely the rotation axis, is provided vertically and the rotary arm 3 is turned horizontally so that conical X-ray beams 1a are locally and horizontally radiated, thus achieving a vertically constructed apparatus requiring small installation area.

The rotation control motor 33 comprises a rotary drive means of the rotary arm 3, uses a motor such as a servo motor which can control its rotational speed and rotational position freely, and is directly and axially attached to the rotation center 3a of the rotary arm 3.

Accordingly, the rotary arm 3 can be turned at a constant velocity or a variable velocity and its rotational position can be known along a time axis so that it is available for taking out X-ray transmitted images by the two-dimensional image sensor 2 in exact timing without runout and thus a local X-ray CT method used in the present invention can be effectively executed.

A hollow part 3b is provided for the rotation center 3a of the rotary arm 3. It is required to make a hollow part for all the members provided on the rotation center 3a in order to have such a hollow part 3b. For this purpose, a servo motor with a hollow axis can be used as a rotation control motor 33.

The hollow part 3b is provided to arrange connection wires between the X-ray generator 1 and the two-dimensional X-ray image sensor 2 suspended from the rotary arm 3 and the operation console 11 of the main frame 10.

The method for arranging the wire becomes a problem in order to provide an electric wring for rotating members. If the connection wire is thus arranged through the rotation center 3a of the rotary arm 3, affection caused by rotation such as twist can be minimized and a preferable effect such as a beautiful appearance can be obtained.

Rotary means C in this embodiment is comprised of a combination of the position control means 31 such as an XY table, the elevation control motor 32 and the rotation control motor 33, however the present invention isn't limited to such construction. As the most easiest construction, the center 3a of the rotary arm 3 may be manually operated by a handle so as to position appropriately.

The object holding means 4 is provided with a head holding means 4a, a chair 4b having the head holding means 4a at the top thereof, and an object positioning mechanism 41. The object positioning mechanism includes a holding means control motor 41a for moving the head holding means 4a vertically, a back tilt control motor for controlling the tilting of the back of the chair 4b, a movable table (not shown) on which the chair 4b is placed and which linearly moves in X-axis direction by an X-axis control motor 41c, in Y-axis direction by a Y-axis control motor 41d and in Z-axis direction by a Z-axis control motor 41e respectively.

The X-axis, the Y-axis, and the Z-axis linearly moving table is constructed with well known cross roller guides and a combination of typical bearings and guides so as to be movable linearly in an accurate manner. While a rack-and-pinion method, a ball screw system or a general screw axis is applied for the X-axis, Y-axis and Z-axis linearly moving table by means of the motors 41c–41e as a driving source, an accurately positioning method is desirable.

The object O sits on the chair 4b and the position of the head holding means 4a is adjusted. Then the head of the object O is secured and the center 3a of the rotary arm 3 and the center Qa of the virtual local area Q in the object O are aligned by means of the object positioning mechanism 41. Further, the rotary arm 3 is turned during X-ray radiation and also the center 3a is simultaneously moved. Otherwise, the rotation center 3a is fixed and alternatively the chair 4b is horizontally moved to move the object O.

Suitable positioning for imaging can be done while the object sits on the chair, thereby achieving an apparatus which is gentle for the object.

Arithmetic processing means D includes a processor operable at high speed for image processing and analysis. A predetermined processing is executed after the X-ray transmission image produced on the two-dimensional image sensor 2 is preprocessed so that three-dimensional X-ray absorption coefficient data in the object through which X-rays are transmitted are calculated. Furthermore, computation such as projection of the data on a projection plane is executed, then an X-ray projection image or a panoramic X-ray image is shown on the display means E and is stored in a required storage means as an image information.

The arithmetic processing means D may be executed sequentially during radiation or may be executed if necessary after radiation.

The main frame 10 is a structure supporting the entire X-ray apparatus 20 and will be detailed hereinafter. The operation console 11 controls the apparatus 20 entirely and executes several control commands receiving input from the operation panel 12. Input and operation required for setting the apparatus 20 are executed by the operation panel 12.

Figure 19:
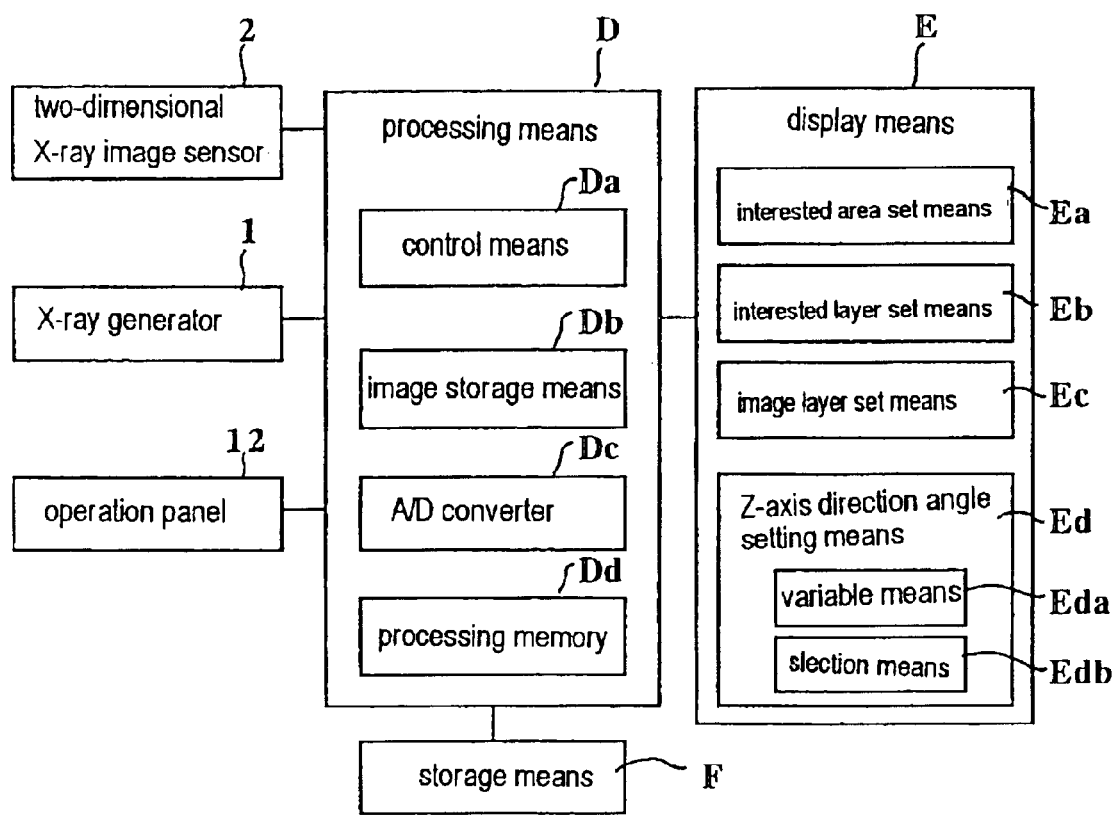
FIG. 19 is a block diagram showing an image signal processing system of an X-ray CT apparatus according to the present invention.

FIG. 19 is a block diagram showing an image signal processing system of an X-ray CT apparatus according to the present invention.

This system includes the arithmetic processing means D as a main part, the X-ray generator 1, the two dimensional X-ray image sensor 2, the operation panel 12, the display means E, and the storage means F, all of which are connected with the arithmetic processing means D. The arithmetic processing means D is provided with a control means Da, an image storage means Db, an A/D converter Dc, and a processor memory Dd.

Such an arithmetic processing means D is constructed with a micro processor for image processing.

The X-ray transmitted image data received from the two dimensional X-ray image sensor (detector) 2 are converted into digital signals by the A/D converter Dc and the digitalized image data are stored in the image storage means Db. Plural image data in the image storage means Db are stored in the processor memory Dd. Calculation of three dimensional X-ray absorption coefficient data by backprojection corresponding to an selected projection mode and operation such as projection of the data on a projection plane are executed for the stored data to produce X-ray projection images and X-ray panoramic images.

These images are shown on the display means E and the three dimensional X-ray absorption coefficient data, the X-ray projection image data, the X-ray panoramic image data are stored in the storage means F if necessary. The obtained three dimensional X-ray absorption coefficient data may be stored in the image storage means Db associated with the original image data.

The display means E includes an interested area setting means Ea for setting a projection interested area and a projection interested layer, an interested layer selection means Eb for selecting a projection interested layer, a projection plane setting means Ec for setting a projection plane, and an angle setting means in a Z-axis direction Ed for setting an angle of a projection plane in a Z-axis direction. The angle setting means in a Z-axis direction Ed has a variable means Eda for variably setting an angle in stepless and a selection means Edb for selecting an angle from plural angles, by either of which the angle of the projection plane in a Z-axis direction can be set.

After the three dimensional X-ray absorption coefficient data are calculated, on the display means E, a projection interested area and a projection interested layer are set by the interested area setting means Ea, an interested layer is appropriately selected by the interested layer selection means Eb, and a projection plane is sequentially set by the projection plane setting means Ec and the angle setting means Ed, producing an X-ray projection image. Thus produced X-ray projection images are displayed in array, in sequence or in continuous so that the object is displayed in a rotational manner (in a manner that the object is rotated).

Hard disc apparatus, a magneto-optic disc apparatus and a frame memory are used for an image storage means Db and a storage means F.

Figure 21:
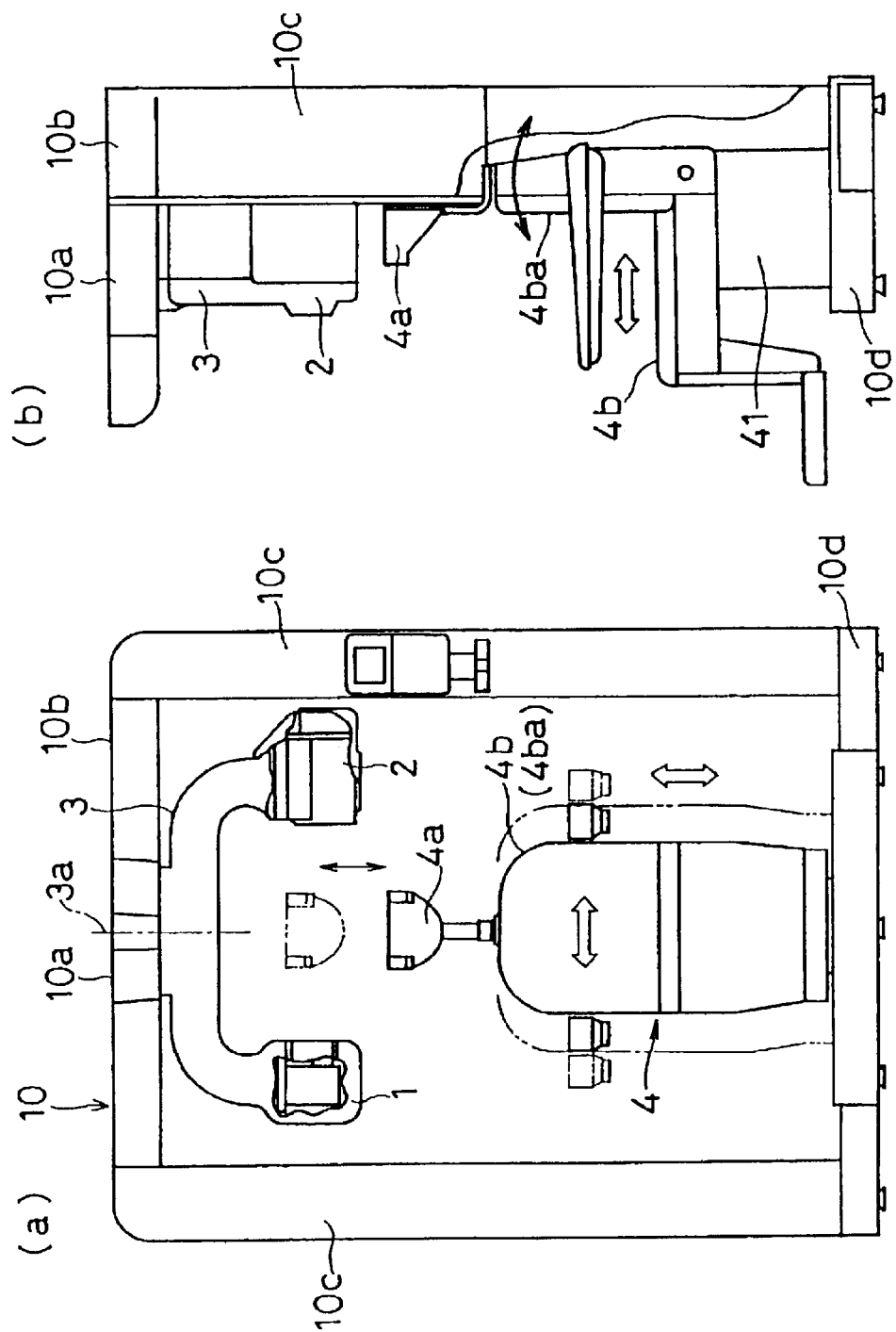
FIG. 21a is a detailed front view of the apparatus of FIG. 20.
FIG. 21b is its side view.

FIG. 20 is an outline view showing one example of an X-ray CT apparatus of the present invention. FIG. 21a is a detailed front view of the apparatus of FIG. 20 and FIG. 21b is its side view.

The main frame 10 which is formed like a gate and is highly rigid structure is designed to support the entire X-ray CT apparatus 20.

The main frame 10 has an arm 10a for rotatably supporting the rotary arm 3 suspending the X-ray generator 1 and the two-dimensional X-ray imaging sensor 2 in opposed condition, a pair of lateral beams 10b securely supporting a base end of the arm 10a, a pair of vertical beams 10c supporting the lateral beams 10b, and a base 10d on which a pair of vertical beams 10c are securely placed and which is a base of the entire apparatus 20.

A highly rigid steel material is used for the members of the main frame 10 and braces and angular reinforcing members are appropriately used for resisting deformation so as not to vary the rotation center 3a of the rotary arm 3 during rotation.

The main frame 10 is constructed not to cause rotary deflection of the rotary arm 3, thereby it is applicable for the X-ray CT apparatus which requires no rotary deflection.

The operation panel 12 is arranged on the surface of the vertical beam 10c of the main frame 10 and where an operator easily uses it while standing. On the object positioning mechanism 41 as explained referring to FIG. 19, the chair 4b of the object holding means 4 is placed in such a manner that the chair 4b is moved in an X-direction, a Y-direction, or a Z-direction, namely in back and forth, vertically and in up and down respectively, and the back 4ba of the chair 4b is tilted so as to hold the head of the object O being tilted.

The display means E constructed with a monitor such as CRT and the arithmetic processing means D is comprised of a personal computer. Programs stored in the recording medium H such as a hard disc, a floppy disc, MO, CD, CDR and DVD are read out to be executed, and data are read in or read out.

A program to achieve the display methods of X-ray projection images for medical use according to the present invention can be stored in the recording medium H. If such a recording medium H is read in the X-ray CT apparatus having the above-mentioned processing means, several display methods of X-ray projection images for medical use according to the present invention can be achieved.

Figure 22:
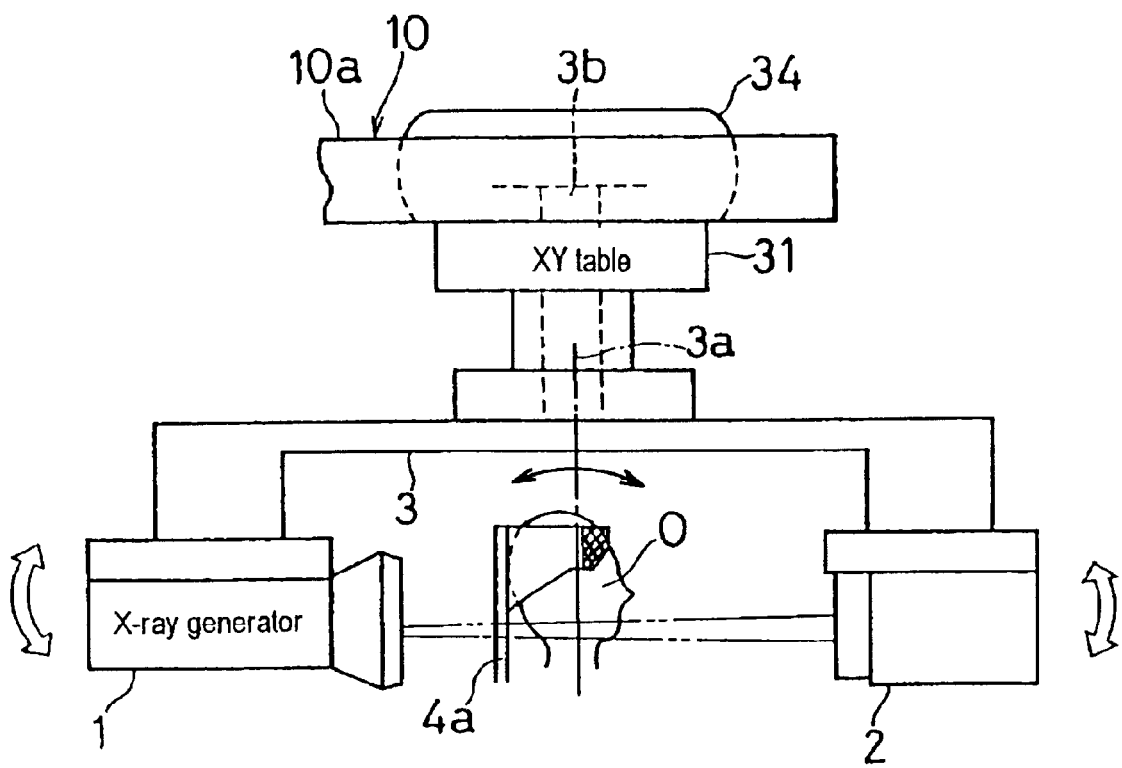
FIG. 22 shows a diagrammatic configuration of a direction setting means of a rotation axis and a setting means of an object supporting direction provided for an X-ray CT apparatus according to the present invention.

FIG. 22 shows a diagrammatic configuration showing a direction setting means of a rotation axis and an object tilting means provided for an X-ray CT apparatus according to the present invention. This figure is further comprised of a rotation axis direction setting means 34 in addition to the basic construction shown in FIG. 20 and FIG. 21.

The rotation axis direction setting means 34 supports the XY table 31 bracing the rotary arm 3 inclinably against the arm 10a of the main frame 10 in such a manner that the center 3a of the rotary arm 3, namely the axial direction of the rotation axis, is inclined into an outlined arrow in the figure against a rising direction of the object O. The head holding means 4a fixes the head of the object O and the head is tilted into an arrow with a solid line by tilting the back 4ba of the chair 4b having the head holding means 4a.

This embodiment shows an X-ray CT apparatus supporting the object substantially vertically. However, the apparatus may be constructed to support the object horizontally for a bed-ridden patient like a prior art, if large occupied area is allowed. Further, a rotary arm is constructed as one arm type in the figures, however, a ring like arm may be used like a prior CT apparatus and an X-ray generator and an X-ray sensor may be provided at both ends so as to be opposed.

INDUSTRIAL APPLICABILITY

1. According to the display method of X-ray projection images for medical use, without using three dimensional X-ray absorption coefficient data obtained by an X-ray CT as it is for constructing an X-ray projection image, three dimensional X-ray absorption coefficient data are extracted on an image layer having a predetermined thickness in a direction perpendicular to an X-ray radiation plane, namely on the image wherein three dimensional X-ray absorption coefficient data are seen from a rotation axial direction of X-ray radiation, and a projection interested area to construct an X-ray projection image is set.

A projection plane to be projected with an X-ray projection image is set to be a flat surface intersecting a radiation plane, in particular substantially perpendicular to an X-ray radiating direction. And an X-ray projection image is obtained by projecting three dimensional X-ray absorption coefficient data in the projection interested area with respect to the projection plane and the obtained X-ray projection image is displayed. In such a manner, three dimensional X-ray absorption coefficient data existing in a direction substantially along the X-ray radiating direction so that clear images can be obtained. In addition, three dimensional X-ray absorption coefficient data are projected on the flat projection plane. Therefore, exemplifying a dental arch, images seen from a projecting direction perpendicular to the projection plane can be obtained and they are easily comprehensive images by intuition for dental diagnosis.

Further, perspectively observable image like the dental arch, namely an object to be examined, is turned are obtained by sequentially obtaining and displaying X-ray projection images by rotating the projecting direction, that is the projection plane, thus obtaining highly comprehensive and highly advantageous images for diagnosis.

Therefore, when this display method is applied to the three dimensional X-ray absorption coefficient data obtained by a method wherein the local X-ray CT method is applied to panoramic images, both effects are multiplied so that several advantages of a local X-ray CT method and apparatus can be used.

2. Comparing with the above-mentioned method 1, the display method of X-ray projection images for medical use in other embodiment is characterized in that not only one X-ray projection image obtained by the above-mentioned method is shown but also plural X-ray projection images can be shown in array. Therefore, in addition to the effects of above-mentioned, X-ray projection images in which an object such as a dental arch is seen from different directions can be compared each other and be compared in a list to select an image required for diagnosis because of such plural displaying, therefore this method is convenient.

3. Comparing with the above-mentioned method 1, the display method of X-ray projection images for medical use can show the object in a rotational manner by continuously showing the X-ray projection images obtained by the method 1 while changing the projecting directions. Therefore, in addition to the effects of 1, even if the display screen is limited, the X-ray projection images of an object such as a dental arch can be continuously compared to select a necessary image for diagnosis because of the continuous rotary display of the X-ray projection images which are easily comprehended by intuition. Accordingly, this method is convenient.

4. Comparing with the method 1, the display method of X-ray projection images for medical is characterized in that the projection interested area is in advance divided into several projection interested layers neighboring each other considering an X-ray radiating direction, three dimensional X-ray absorption coefficient data in optional one layer or the neighboring plural layers are used and thus obtained X-ray projection images are selectively displayed. Therefore, in addition to the effects of 1, if the projection interested area is a dental arch area, the projection interested layer is a layer neighboring each other from a cheek to a tongue. Thus knowing the area or the layer used for constructing the X-ray projection image of the dental root, the position of the root where in a cheek to a tongue can be understood.

5. Comparing with the method 1, the display method of X-ray projection images for medical use combines the display in array in 2, the continuous display in 3 and the display method in 4 wherein the projection interested area is divided into plural projection interested layers and the X-ray projection images obtained by using the three dimensional X-ray absorption coefficient data in the projection interested layer are selectively shown. Therefore, the effects of 2, 3 and 4 are multiplied in addition to the effect of 1.

6. The display method of X-ray projection images for medical use particularly defines the projection interested area of the above-mentioned display methods into a dental arch area. Therefore, the above-mentioned effects can be achieved for displaying the X-ray projection image of the dental arch area.

7. According to the display method of X-ray projection images for medical use, in case that the projection interested area is a dental arch area, the projection plane is arranged to be parallel to a rising direction of a tooth or a projecting direction of a dental root in the dental arch area. The rising direction of a tooth isn't always a direction perpendicular to an articulation surface of the dental arch, namely a direction orthogonal to a projecting direction of X-ray. Therefore, if a projection plane is normally set, an X-ray projection image showing a rising direction of a dental tooth at an angle is obtained and the accurate length of the tooth in a rising length isn't shown in the image. However, if the projection plane is parallel to the rising direction of the tooth, the rising direction of the tooth is accurately shown on the image, thus improving convenience.

8. In the display method of X-ray projection images for medical use, when the projection interested area is a dental arch area, a rotation center of a projection plane which is rotatively moved is fixed. In such a manner, even in a method a local X-ray CT method is applied to panoramic images, when a rotation center of a rotary arm is fixed at the time of projection, control is facilitated. Otherwise, a rotary arm may be moved in case of projection.

9. In the display method of X-ray projection images for medical use, a rotation center of the projection plane is transferred in a predetermined pattern in the above-mentioned display methods 5–7 wherein the projection interested area is a dental arch area. In this case, if a rotation center of a rotary arm isn't fixed during projection when the local X-ray CT method is applied to panoramic images, clear X-ray projection images can be obtained by conforming radiating conditions and projecting conditions. If a rotation center of a rotary arm is fixed during projection, obstacle shades such as a neck bone can be eliminated.

10. In the display method of X-ray projection images for medical use, a method characterized in that a projection interested area is set and three dimensional X-ray absorption coefficient data in the area are projected is applied to produce X-ray panoramic images. Therefore, images without obstacle shades are also obtained for X-ray panoramic images.

The projection plane for producing X-ray panoramic images is curved unlike the flat projection plane in 1. If an object is a dental arch, the curved projection plane is a curved plane binding the centerline of the dental arch. These X-ray panoramic images aren't only used for a dental arch in the dental field, but they include X-ray projection images used for other medical field such as diagnosis of rib bone in addition to an otolaryngology area, a dental surgery area, and a maxillo facial area to obtain images by sequentially projecting on the curved projection plane.

11. In the display method of X-ray projection images for medical use, the display method characterized in that a projection interested area is divided into projection interested layer and the X-ray projection images obtained by three dimensional X-ray absorption coefficient data in the projection interested layer are selectively displayed is applied to X-ray panoramic images. Therefore, as to X-ray panoramic images, where a dental root exists from a cheek to a tongue can be understood.

12. The display apparatus of X-ray projection images for medical use is to achieve the above-mentioned display methods 1 and 2. Therefore, it has the same effect as 1 and 2. Further, the X-ray projection images which have been once stored are read out to be displayed so that the X-ray projection images aren't required to be produced each time. Therefore, the X-ray projection images can be promptly displayed, thus preventing an operator from being annoyed to wait for a display required for diagnosis.

13–15. The display apparatus of X-ray projection images for medical use is to achieve the above-mentioned display methods 3–5. Therefore, it has the same effects as 3–5. Further, the X-ray projection images which have been once stored are read out to be displayed so that the X-ray projection images aren't required to be produced each time. Therefore, the X-ray projection images can be promptly displayed, thus preventing an operator from being annoyed to wait for display required for diagnosis.

16–21. The display apparatus of X-ray projection images for medical use is to achieve the above-mentioned display methods 6–11. Therefore, it has the same effects as 6–11.

22. In the X-ray CT apparatus for medical use, an image construction means having an X-ray generator and an X-ray detector is combined with the display method 15. It achieves the display method 5 and has the effect of 5 as a medical X-ray CT apparatus.

23. The X-ray CT apparatus for medical use achieves the display method in 6 and has the effect of 6.

24. The X-ray CT apparatus for medical use is for obtaining X-ray panoramic images, achieves the display methods in 10 and 11 and has the effects of 10 and 11.

25. According to the X-ray CT apparatus for medical use, in addition to the effects of the apparatus 22–24, a rotation center of a rotary arm is moved, not being fixed during X-ray radiation. For example if the a rotation center of radiated X-rays is moved along an envelope curve, X-rays can be radiated on a dental arch from a direction substantially perpendicular to a tooth, thereby achieving valuable images for diagnosis without obstacle shades.

26. According to the X-ray CT apparatus for medical use, in addition to the effects of the apparatus 22–24, comparing with the apparatus 25, a rotation center of a rotary arm is fixed, an object is gradually moved during X-ray radiation, thus a rotation center of the radiated X-rays is relatively moved. In addition to the same effect as 25, more precise X-ray radiation can be accomplished because the rotation center of the rotary arum isn't moved. More accurate three dimensional X-ray absorption coefficient data can be obtained from thus obtained transmitted data and as the result more accurate X-ray projection image can be also obtained.

27. According to the X-ray CT apparatus for medical use, in addition to the effects of the apparatus 22–26, X-rays are radiated while varying a rotational speed of a rotary arm. Therefore, density compensation can be executed according to the radiated tooth, thus obtaining better X-ray projection images.

28. According to the X-ray CT apparatus for medical use, in addition to the effects of the apparatus 22–27, like the apparatus 27, density compensation can be executed according to the radiated tooth, thus obtaining better X-ray projection images.

29. According to the X-ray CT apparatus for medical use, in addition to the effects of the apparatus 22–28, inclination of a chair for holding an object is adjusted in such a manner that an X-ray radiating direction becomes, for example, perpendicular to a rising direction of a tooth, thereby obtaining transmitted images without inclining the rising direction of a tooth. Accordingly, better X-ray projection images reflecting the rising direction of a tooth can be obtained.

30–40. The recording medium saves a program to achieve the display method 1–11. When the medium reads the program and is attached to an apparatus capable of carrying out the program, the display method 1–11 is achieved and the effect of 1–11 is brought out.

What is claimed is:

1. A display method of an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined, said method comprising the steps of:

a) displaying an image layer of said object with a predetermined thickness extending perpendicular to a radiation plane defined by rotational irradiation of an X-ray beam for said X-ray Ct;

b) setting a projection interested area to construct the X-ray projection image of said object on said image layer, said projection interested area being comprised of said three dimensional X-ray absorption coefficient data;

c) producing the X-ray projection image with respect to a projection plane intersecting said radiation plane by projecting said three dimensional X-ray absorption coefficient data existing in said projection interested area by further setting said projection plane on said image layer; and d) displaying thus obtained X-ray projection image for medical use.

2. A display method of an X-ray projection image for medical use, which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined, said method comprising the steps of:

a) displaying an image layer of said object with a predetermined thickness extending perpendicular to a radiation plane defined by rotational irradiation of an X-ray beam for said X-ray CT;

b) setting a projection interested area to construct the X-ray projection image of said object on said image layer, said projection interested area being comprised of said three dimensional X-ray absorption coefficient data;

c) producing the X-ray projection image with respect to a projection plane intersecting said radiation plane by projecting said three dimensional X-ray absorption coefficient data existing in said projection interested area by further setting said projection plane on said image layer; and d) displaying in array thus obtained X-ray projection image for medical use.

3. A display method of an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined, said method comprising the steps of:

a) displaying an image layer of said object with a predetermined thickness extending perpendicular to a radiation plane defined by rotational irradiation of an X-ray beam for said X-ray CT;

b) setting a projection interested area to construct the X-ray projection image of said object on said image layer, said projection interested area being comprised of said three dimensional X-ray absorption coefficient data;

c) producing the X-ray projection image with respect to a projection plane intersecting said radiation plane by projecting said three dimensional X-ray absorption coefficient data existing in said projection interested area by further setting said projection plane on said image layer; and d) displaying in sequence thus obtained X-ray projection image for medical use.

4. A display method of an X-ray projection image for medical use which is obtained by rotating a direction in which the X-ray projection image is to be projected based on three dimensional X-ray absorption coefficient data previously produced by an X-ray CT, the X-ray CT being earned out by turning an X-ray generator and an X-ray detector, facing each other, around an object to be examined, said method comprising the steps of:

a) displaying an image layer of said object with a predetermined thickness extending perpendicular to a radiation plane defined by rotational irradiation of an X-ray beam for said X-ray CT;

b) setting a projection interested area to construct the X-ray projection image of said object on said image layer, said projection interested area being comprised of said three dimensional X-ray absorption coefficient data;

c) dividing said projection interested area into plural projection interested layers neighboring each other in an X-ray radiating direction;

d) producing the X-ray projection image with respect to a projection plane intersecting said radiation plane by projecting said three dimensional X-ray absorption coefficient data existing in said projection interested area by further setting said projection plane on said image layer; and e) displaying selectively thus obtained X-ray projection image for medical use.

5. A display method of an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined, said method comprising the steps of:

a) setting a curved projection interested area to construct the X-ray projection image of the object on an image layer with an extending predetermined thickness perpendicular to a radiation plane defined by rotational irradiation of an X-ray beam for said X-ray CT, said projection interested area being comprised of one of said three dimensional X-ray absorption coefficient data;

b) dividing said projection interested area into plural projection interested layers neighboring each other in an X-ray radiating direction;

c) producing the X-ray projection image by projecting said three dimensional X-ray absorption coefficient data existing in the optional one projection interested layer or the plural projection interested layers with respect to a projection plane intersecting said radiation plane; and d) displaying the object in a rotational manner by showing selectively in array or in sequence thus obtained X-ray projection image for medical use.

6. The displayed method of an X-ray projection image for medical use as set forth in claim 5, wherein said projection interested area is a dental arch area.

7. The display method of an X-ray projection image for medical use as set forth in claim 6, wherein said projection plane is arranged to be parallel to a rising direction of a tooth or a projecting direction of a dental root.

8. The display method of an X-ray projection image for medical use as set forth in any one of claims 5–7, wherein a rotation center of said projection plane which moves rotatively is fixed.

9. The display method of an X-ray projection image for medical use as set forth in any one of claims 5–7, wherein a rotation center of said projection plane which moves rotatively is moved in a predetermined form.

10. A display method of an X-ray projection image for medical use for showing an X-ray panoramic image based on three dimensional X-ray absorption coefficient data previously produced by an X-ray CT, the X-ray CT being carried out by turning an X-ray generator and an X-ray detector, facing each other, around an object to be examined, said method comprising the steps of:

a) displaying an image layer of said object with a predetermined thickness extending perpendicular to a radiation plane defined by rotational irradiation of an X-ray beam for said X-ray CT;

b) setting a projection interested area to construct the X-ray projection image of said object on said image layer, said projection interested area being comprised of said three dimensional X-ray absorption coefficient data;

c) producing the X-ray panoramic image by projecting said three dimensional X-ray absorption coefficient data existing in said projection interested area on a projection plane; and d) displaying thus obtained X-ray panoramic image for medical use.

11. A display method of an X-ray projection image for medical use for showing an X-ray panoramic image based on three dimensional X-ray absorption coefficient data previously produced by an X-ray CT, the X-ray CT being carried out by turning an X-ray generator and an X-ray detector, facing each other, around an object to he examined, said method comprising the steps of:

a) displaying an image layer of said object with a predetermined thickness extending perpendicular to a radiation plane defined by rotational irradiation of an X-ray beam for said X-ray CT;

b) setting a projection interested area to construct the X-ray projection image of said object on said image layer, said projection interested area being comprised of said three dimensional X-ray absorption coefficient data;

c) dividing said projection interested area into plural projection interested layers neighboring each other in an X-ray radiating direction;

d) producing the X-ray panoramic image by projecting said three dimensional X-ray absorption coefficient data existing in the optional one projection interested layer or the plural projection interested layers on a projection plane; and e) displaying selectively thus obtained X-ray panoramic image for medical use.

12. A display apparatus of an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined, wherein:

an image layer of said object with a predetermined thickness extending perpendicular to a radiation plane defined by rotational irradiation of an X-ray beam for said X-ray CT is displayed and wherein a projection interested area to construct an X-ray projection image of said object is set on said image layer, said projection interested area being comprised of said three dimensional X-ray absorption coefficient data, whereby said X-ray projection image with respect to a projection plane intersecting said radiation plane is produced by projecting said three dimensional X-ray absorption coefficient data existing in said projection interested area by further setting said projection plane on said image layer; and said display apparatus comprising:
  a) a memory means for storing thus obtained X-ray projection image; and
  b) a display means for showing in array thus obtained X-ray projection image read from said memory means.

13. A display apparatus of an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined, wherein:

a projection interested area to construct the X-ray projection image of the object is set on an image layer with an extending predetermined thickness perpendicular to a radiation plane defined by rotational irradiation of an X-ray beam for said X-ray CT, said projection interested area is comprised of one of said three dimensional X-ray absorption coefficient data, and the X-ray projection image is produced by projecting said three dimensional X-ray absorption coefficient data existing in said projection interested area with respect to a projection plane intersecting said radiation plane; and said display apparatus comprising:
  a) a memory means for stating thus obtained X-ray projection image; and
  b) a display means for showing the object in a rotational manner by sequentially showing thus obtained X-ray projection image read out of said memory means.

14. A display apparatus of an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined, wherein:

an image layer of said object with a predetermined thickness extending perpendicular to a radiation plane defined by rotational irradiation of an X-ray beam for said X-ray CT is displayed and wherein a projection interested area to construct an X-ray projection image of said object is set on said image layer, said projection interested area being comprised of said three dimensional X-ray absorption coefficient data, whereby said X-ray projection image with respect to a projection plane intersecting said radiation plane is produced by projecting said three dimensional X-ray absorption coefficient data existing in said projection interested area by further setting said projection plane on said image layer; and said display apparatus comprising:
  a) a memory means for storing thus obtained X-ray projection image; and
  b) a display means selectively showing said X-ray projection interested area read out of said memory means or said X-ray projection image.

15. A display apparatus of an X-ray projection image for medical use which is obtained by rotating a direction in which the X-ray projection image is to be projected based on three dimensional X-ray absorption coefficient data previously produced by an X-ray CT, the X-ray CT being carded out by turning an X-ray generator and an X-ray detector, facing each other, around an object to be examined, wherein:

a projection interested area to construct the X-ray projection image of the object is set on an image layer with an extending predetermined thickness perpendicular to a radiation plane defined by rotational irradiation of an X-ray beam for said X-ray CT, said projection interested area is comprised of one of said three dimensional X-ray absorption coefficient data, and said projection interested area is divided into plural projection interested layers neighboring each other in an X-ray radiating direction; and said display apparatus comprising:
  a) a selection means for selecting any one projection interested layer or plural projection interested layers neighboring each other;
  b) a memory means for storing the X-ray projection image produced by projecting the three dimensional X-ray absorption coefficient data existing in the selected projection interested layer with respect to a projection plane intersecting said radiation plane; and
  c) a display means showing the object in a rotational manner by selectively in array or in sequence showing said X-ray projection image read out of said memory means.

16. The display apparatus of an X-ray projection image for medical use as set forth in any one of claims 12–15, wherein said projection interested area is a dental arch area.

17. The display apparatus of an X-ray projection image for medical use as set forth in claim 16, wherein said projection plane is arranged to be parallel to a rising direction oh tooth or a projecting direction of a dental root.

18. The display apparatus of an X-ray projection image for medical use as set forth in anyone of claims 12–15, wherein a rotation center of said projection plane which moves rotatively is fixed.

19. The display apparatus of an X-ray projection image for medical use as set forth in any one of claims 12–15, wherein a rotation center of said projection plane which moves rotatively is moved in a predetermined form.

20. A display apparatus of an X-ray projection image for showing an X-ray panoramic image based on three dimensional X-ray absorption coefficient data previously produced by an X-ray CT, the X-ray CT being carried out by turning an X-ray generator and an X-ray detector, facing each other, around an object to be examined wherein:

an image layer of said object with a predetermined thickness extending perpendicular to a radiation plane defined by rotational irradiation of an X-ray beam for said X-ray CT is displayed, and wherein a projection interested area to construct the X-ray projection image of the object is set on said image layer, said projection interested area being comprised of said three dimensional X-ray absorption coefficient data, whereby the X-ray panoramic image with respect to a projection plane intersecting said radiation plane is produced by projecting said three dimensional X-ray absorption coefficient data existing in said projection interested area on said projection plane; and said display apparatus comprising:
  a) a memory menus for storing thus obtained X-ray panoramic image; and
  b) a display means for showing thus obtained X-ray panoramic image read from said memory means.

21. A display apparatus of an X-ray projection image for showing an X-ray panoramic image based on three dimensional X-ray absorption coefficient data previously produced by an X-ray CT, the X-ray CT being carried out by turning an X-ray generator and an X-ray detector, facing each other, around an object to be examined wherein:

an image layer of said object with a predetermined thickness extending perpendicular to a radiation plane defined by rotational irradiation of an X-ray beam for said X-ray CT is displayed, and wherein a projection interested area to construct the X-ray projection image of said object is set on said image layer, and wherein said projection interested area is divided into plural projection interested layers neighboring each other in an X-ray radiating direction, said projection interested area being comprised of said three dimensional X-ray absorption coefficient data, whereby the X-ray panoramic image is produced by projecting said three dimensional X-ray absorption coefficient data existing in the optional one projection interested layer or the plural projection interested layers on a projection plane; and said display apparatus comprising:
  a) a memory means for storing thus obtained X-ray panoramic image; and
  b) display means for selectively showing said X-ray panoramic image read out of said memory means.

22. An X-ray CT apparatus for medical use having a rotary arm with an X-ray generator and an X-ray detector facing each other for radiating X-rays around an object to be examined and having an image construction means which constructs an X-ray projection image on a desired projection plane based on the object's three dimensional X-ray absorption coefficient data obtained by the output of the X-ray detector; wherein a projection interested area to construct the X-ray projection image of the object in set on an image layer with an extending predetermined thickness perpendicular to a radiation plane defined by rotational irradiation of an X-ray beam, said projection interested area is comprised of one of said three dimensional X-ray absorption coefficient data, and said projection interested area is divided into plural projection interested layers neighboring each other in an X-ray radiating direction; and said X-ray CT apparatus comprising:
  a) a selection means for selecting one projection interested layer or plural projection interested layers neighboring each other;
  b) a memory means for storing the X-ray projection image produced by projecting the three dimensional X-ray absorption coefficient data existing in said selected projection interested layer on a projection plane intersecting said radiation plane; and
  c) a display means showing the object in rotational manner by showing selectively or in sequence said X-ray projection image read out of said memory means.

23. The X-ray CT apparatus for medical use as set forth in claim 22, wherein said projection interested area is a dental arch area.

24. An X-ray CT apparatus for medical use having a rotary arm with an X-ray generator and an X-ray detector facing each other for radiating X-rays around an object to be examined and having an image construction means which constructs an X-ray panoramic image on a desired projection plane based on the object's three dimensional X-ray absorption coefficient data obtained by the output of the X-ray detector; wherein an image layer of said object with a predetermined thickness, extending perpendicular to a radiation plane defined by rotational irradiation of an X-ray beam is displayed, and wherein said projection interested area to construct an X-ray projection image of said object is set on said image layer, said projection interested area being comprised of said three dimensional X-ray absorption coefficient data, whereby said projection interested area is divided into plural projection interested layers neighboring each other in an X-ray radiating direction; and said X-ray CT apparatus comprising:
  a) a selection means for selecting one projection interested layer or plural projection interested layers neighboring each other;
  b) a memory means for storing the X-ray panoramic image obtained by projecting the three dimensional X-ray absorption coefficient data in the selected projection interested layer on a projection plane; and
  c) display means for showing the X-ray panoramic image in array read out of said memory means.

25. The X-ray CT apparatus for medical use as set forth in any one of claims 22–24, wherein a rotation center of said rotary arm is moved during X-ray radiation by the minute.

26. The X-ray CT apparatus for medical use as set forth in any one of claims 22–24, wherein a chair holding said object is moved accompanied with a turning position of said rotary arm during X-ray radiation.

27. The X-ray CT apparatus for medical use as set forth in claim 22 or 24, wherein a rotational velocity of said rotary arm is varied during X-ray radiation.

28. The X-ray CT apparatus for medical use as set forth in claim 22 or 24, wherein an X-ray tube voltage and/or an X-ray tube current is/are varied according to a rotational position of said rotary arm.

29. The X-ray CT apparatus for medical use as set forth in claim 22 or 24, wherein a chair holding the object is adjustably tilted.

30. A recording medium for recording a program to achieve a method of displaying an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined; said program comprising the steps of:
 a) displaying an image layer of said object with a predetermined thickness extending perpendicular to a radiation plane defined by rotational irradiation of an X-ray beam for said X-ray CT;
 b) setting a projection interested area to construct the X-ray projection image of said object on said image layer, said projection interested area being comprised of said three dimensional X-ray absorption coefficient data;
 c) producing the X-ray projection image with respect to a projection plane intersecting said radiation plane by projecting said three dimensional X-ray absorption coefficient data existing in said projection interested area by further setting said projection plane on said image layer; and
 d) displaying thus obtained X-ray projection image for medical use.

31. A recording medium for recording a program to achieve a method of displaying an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined; said program comprising the steps of:
 a) displaying an image layer of said object with a predetermined thickness extending perpendicular to a radiation plane defined by rotational irradiation of an X-ray beam for said X-ray CT;
 b) setting a projection interested area to construct the X-ray projection image of said object on said image layer, said projection interested area being comprised of said three dimensional X-ray absorption coefficient data;
 c) producing the X-ray projection image with respect to a projection plane intersecting said radiation plane by projecting said three dimensional X-ray absorption coefficient data existing in said projection interested area by further setting said projection plane on said image layer; and
 c) displaying in array thus obtained X-ray projection image for medical use.

32. A recording medium for recording a program to achieve a method of displaying an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and a X-ray detector, facing each other, around an object to be examined, said program comprising the steps of:
 a) setting a projection interested area to construct the X-ray projection image of the object on a image layer with an extending predetermined thickness perpendicular to a radiation plane defined by rotational irradiation of an X-ray beam for said X-ray CT, said projection interested area being comprised of said three dimensional X-ray absorption coefficient data;
 b) producing the X-ray projection image by projecting said three dimensional X-ray absorption coefficient data existing in said projection interested area with respect to a projection plane intersecting said radiation plane; and
 c) displaying the object in a rotational manner by showing in sequence thus obtained X-ray projection image for medical use.

33. A recording medium for recording a program to achieve a method of displaying an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined; said program comprising the steps of:
 a) displaying an image layer of said object with a predetermined thickness extending perpendicular to a radiation plane defined by rotational irradiation of an X-ray beam for said X-ray CT;
 b) setting a projection interested area to construct the X-ray projection image of said object on said image layer, said projection interested area being comprised of said three dimensional X-ray absorption coefficient data;
 c) dividing said projection interested area into plural projection interested layer neighboring each other in an X-ray radiating direction;
 d) producing the X-ray projection image with respect to a projection plane intersecting said radiation plane by projecting said three dimensional X-ray absorption coefficient data existing in the optional one projection interested layer or the plural projection interested layers by further setting said projection plane on said image layer; and
 e) displaying selectively thus obtained X-ray projection image for medical use.

34. A recording medium for recording a program to achieve a method of displaying an X-ray projection image for medical use which is obtained by rotating a direction in which the X-ray projection image is to be projected based on three dimensional X-ray absorption coefficient data previously produced by an X-ray CT, the X-ray CT being carried out by turning an X-ray generator and an X-ray detector, facing each other, around an object to be examined; said program comprising the steps of:
 a) setting a curved projection interested area to construct the X-ray projection image of said object on an image layer with an extending predetermined thickness perpendicular to a radiation plane defined by rotational irradiation of an X-ray beam for said X-ray CT, said projection interested area being comprised of said three dimensional X-ray absorption coefficient data;
 b) dividing said projection interested area into plural projection interested layers neighboring each other in an X-ray radiating direction;
 c) producing the X-ray projection image by projecting said three dimensional X-ray absorption coefficient data existing in the optional one projection interested layer or the plural projection interested layers with respect to a projection plane intersecting said radiation plane; and d) displaying the object in a rotational manner by selectively in array or in sequence showing thus obtained X-ray projection image for medical use.

35. The recording medium as set forth in claim 34, wherein said projection interested area is a dental arch area.

36. The recording medium as set forth in claim 35, wherein said projection plane is arranged to be parallel to a rising direction of a tooth or a projecting direction of a dental root.

37. The recording medium as set forth in any one of claims 30–34, wherein a rotation center of said projection plane which moves rotatively is fixed.

38. The recording medium as set forth in any one of claims 30–34, wherein a rotation center of said projection plane which moves rotatively is moved in a predetermined form.

39. A recording medium for recording a program to achieve a method of displaying an X-ray panoramic image for medical use based on three dimensional X-ray absorption coefficient data previously produced by an X-ray CT, the X-ray CT being carried out by turning and X-ray generator and an X-ray detector, facing each other, around an object to be examined, said program comprising the steps of:

a) displaying an image layer of said object with a predetermined thickness extending perpendicular to a radiation plane defined by rotational irradiation of an X-ray beam for said X-ray CT;

b) setting a projection interested area to construct the X-ray projection image of said object on said image layer, said projection interested area being comprised of said three dimensional X-ray absorption coefficient data;

c) producing the X-ray panoramic image with respect to a projection plane intersecting said radiation plane by projecting said three dimensional X-ray absorption coefficient data existing in said projection interested area by further setting said projection plane on said image layer; and d) displaying thus obtained X-ray panoramic image for medical use.

40. A recording medium for recording a program to achieve a method of displaying an X-ray panoramic image for medical use based on three dimensional X-ray absorption coefficient data previously produced by X-ray CT, the X-ray CT being carried out by turning an X-ray generator and an X-ray detector, facing each other, around an object to be examined, said program comprising the steps of:

a) displaying an image layer of said object with a predetermined thickness extending perpendicular to a radiation plane defined by rotational irradiation of an X-ray beam for said X-ray CT;

b) setting a projection interested area to construct the X-ray projection image of said object on said image layer, said projection interested area being comprised of said three dimensional X-ray absorption coefficient data;

c) dividing the projection interested area into plural projection interested layers neighboring each other in an X-ray radiating direction;

d) producing an X-ray panoramic image by projecting said three dimensional X-ray absorption coefficient data existing in the one optional projection interested layer or the plural projection interested layers with respect to a projection plane; and e) displaying selectively thus obtained X-ray panoramic image for medical use.

* * * * *